United States Patent
Xiao

(10) Patent No.: US 7,481,955 B2
(45) Date of Patent: Jan. 27, 2009

(54) PHOTOCHROMIC MATERIALS COMPRISING METALLOCENYL GROUPS

(75) Inventor: Wenjing Xiao, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 295 days.

(21) Appl. No.: 11/443,938

(22) Filed: May 31, 2006

(65) Prior Publication Data

US 2007/0278460 A1 Dec. 6, 2007

(51) Int. Cl.
- F21V 9/00 (2006.01)
- G02B 5/02 (2006.01)
- G02C 7/10 (2006.01)
- G02F 1/361 (2006.01)
- G03B 11/00 (2006.01)

(52) U.S. Cl. .................. 252/582; 252/586; 544/149; 549/356

(58) Field of Classification Search ......... 252/582–589; 428/500–523, 412, 424.2, 461–463, 441–442
See application file for complete search history.

(56) References Cited

U.S. PATENT DOCUMENTS

| | | | |
|---|---|---|---|
| 3,971,872 A | 7/1976 | LeBoeuf | |
| 4,904,525 A | 2/1990 | Taniguchi et al. | |
| 5,104,692 A | 4/1992 | Belmares | |
| 5,645,767 A | 7/1997 | Van Gemert | |
| 6,025,026 A | 2/2000 | Smith et al. | |
| 6,060,001 A | 5/2000 | Welch et al. | |
| 6,068,797 A | 5/2000 | Hunt | |
| 6,113,814 A | 9/2000 | Gemert et al. | |
| 6,146,554 A * | 11/2000 | Melzig et al. | 252/586 |
| 6,150,430 A | 11/2000 | Walters et al. | |
| 6,187,444 B1 | 2/2001 | Bowles, III et al. | |
| 6,268,055 B1 | 7/2001 | Walters et al. | |
| 6,296,785 B1 | 10/2001 | Nelson et al. | |
| 6,432,544 B1 | 8/2002 | Stewart et al. | |
| 6,436,525 B1 | 8/2002 | Welch et al. | |
| 6,506,488 B1 | 1/2003 | Stewart et al. | |
| 6,531,076 B2 | 3/2003 | Crano et al. | |
| 6,555,028 B2 | 4/2003 | Walters et al. | |
| 6,602,603 B2 | 8/2003 | Welch et al. | |
| 6,916,537 B2 | 7/2005 | Welch et al. | |
| 2003/0165686 A1 | 9/2003 | Blackburn et al. | |
| 2005/0096467 A1 | 5/2005 | Mann et al. | |
| 2005/0151926 A1 | 7/2005 | Kumar et al. | |
| 2007/0145337 A1 * | 6/2007 | Chopra | 252/586 |

FOREIGN PATENT DOCUMENTS

WO WO 03/080595 A1 2/2003

OTHER PUBLICATIONS

Stéphane Anguille, Pierre Brun, Robert Guglielmetti, Yuri P. Strokach, Alexandre A. Ignatin, Valery A. Barachevsky and Michael V. Alfimov, J. Chem. Soc., Perkin Trans. 2, 2001, 639-644. ( by The Royal Society of Chemistry ).*

Pierre Brun, Robert Guglielmetti and Stéphane Anguille, Appl. Organometal. Chem. 2002, 16: 271-276 (by Wiely InterScience).*

Kim, Beon-Kyu et al, U.S. Appl. No. 11/102,279, entitled "Photochromic Materials Having Extended PI-Conjugated Systems And Compositions And Articles Including The Same", filed Apr. 8, 2005.

Xiao, Wenjing et al, U.S. Appl. No. 11/102,280, entitled "Photochromic Materials With Reactive Substituents", filed Apr. 8, 2005.

Anguille et al., "Synthesis and photochromc properties of ferrocenyl substituted benzo- dibenzochromenes" Journal of the Chemical Society, Perkin Transactions 2, No. 4, 2001, pp. 639-644 XP002449350.

P. Brun et al., "Spectrokinetic study of a series of photochromic 2-ferrocenyl-2-methyl[2H]-chromenes" Journal of Photochemistry and Photobiology, A: Chemistry, vol. 15, 2003, pp. 77-82.

Anguille et al., "A thermochromism study in the ferrocenyl-benzopyran series" Applied Organometallic Chemistry, vol. 18, 2004, pp. 67-70, XP002449351.

* cited by examiner

*Primary Examiner*—Lorna M Douyon
*Assistant Examiner*—Bijan Ahvazi
(74) *Attorney, Agent, or Firm*—Frank P. Mallak; Deborah M. Altman

(57) ABSTRACT

Various non-limiting embodiments of the present invention relate to photochromic materials having a metallocenyl group. More particularly, various non-limiting embodiments disclosed herein provide photochromic materials including an indeno-fused naphthopyran, such as an indeno[2',3':3,4]naphtho[1,2-b]pyran, and a metallocenyl group bonded to at least one available position on the indeno-fused naphthopyran. Other non-limiting embodiments disclosed herein provide photochromic composition and photochromic articles, such as but not limited to ophthalmic lens, which include the disclosed photochromic materials and method of making the same.

17 Claims, 4 Drawing Sheets

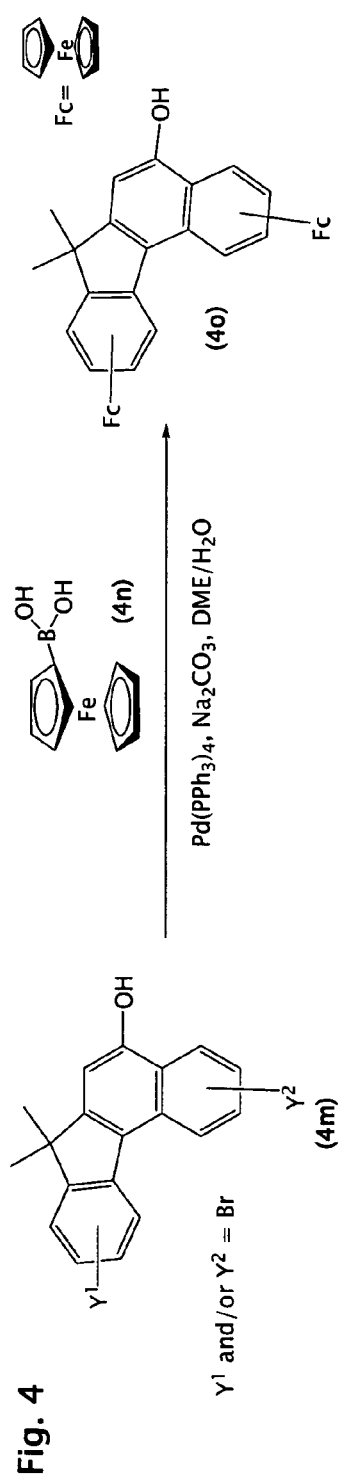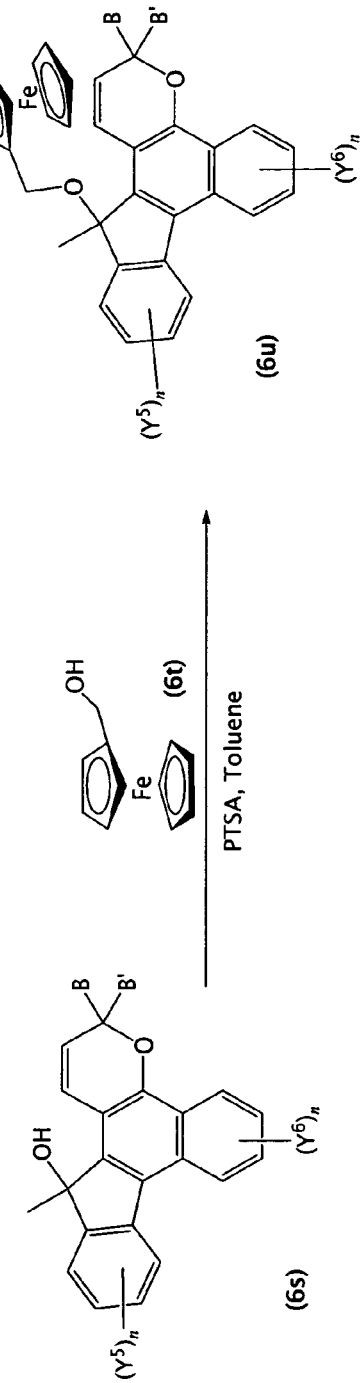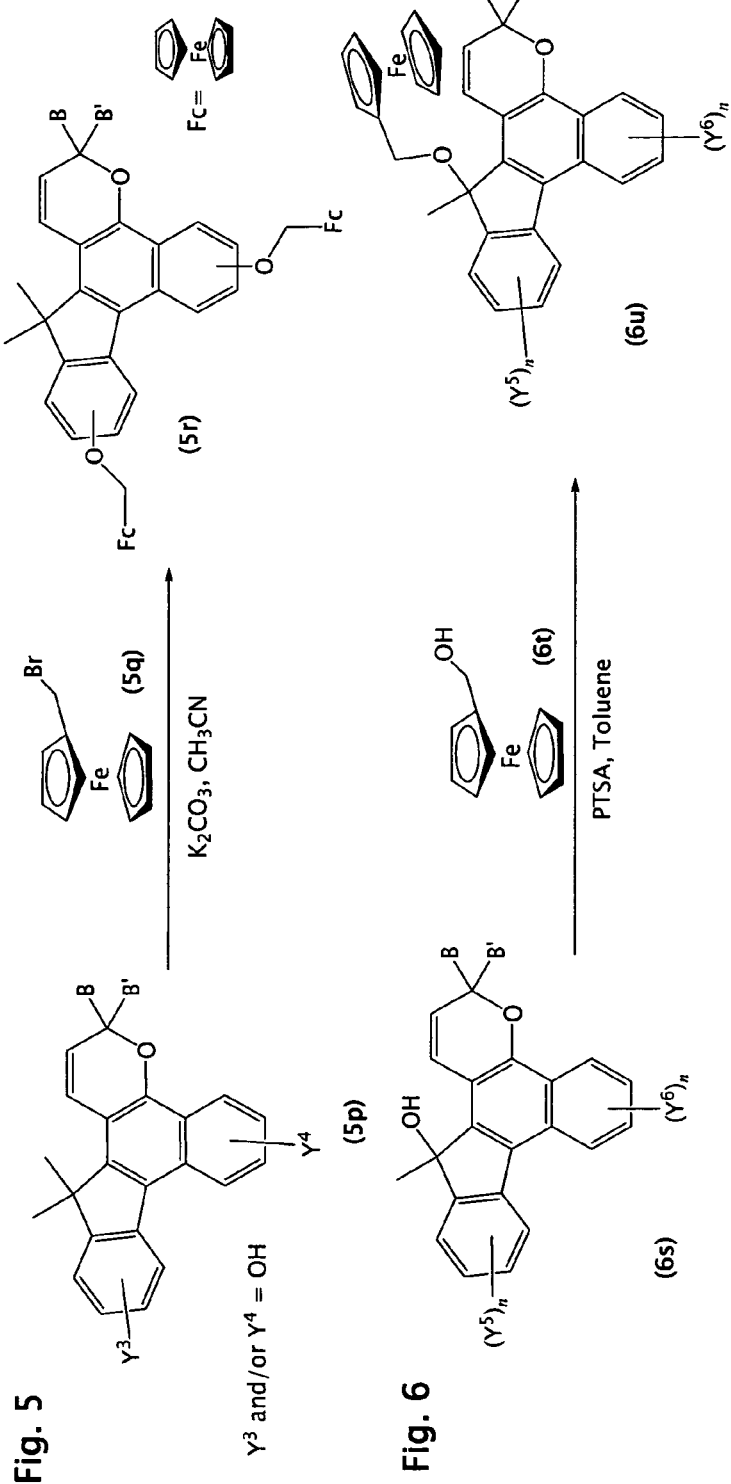
Fig. 4
Fig. 5
Fig. 6

PHOTOCHROMIC MATERIALS COMPRISING METALLOCENYL GROUPS

BACKGROUND

The present invention generally relates to photochromic materials, and more particularly relates to photochromic materials comprising an indeno-fused naphthopyran and a metallocenyl group bonded to the indeno-fused naphthopyran. The present invention further relates to photochromic compositions and articles that comprise such photochromic materials.

Photochromic materials undergo a transformation from one form (or state) to another in response to certain wavelengths of electromagnetic radiation, with each form having a characteristic absorption spectrum for visible radiation. For example, thermally reversible photochromic materials are capable of transforming from a ground-state form to an activated-state form in response to actinic radiation, and reverting back to the ground-state form in response to thermal energy and in the absence of the actinic radiation. As used herein, the term "actinic radiation" refers to electromagnetic radiation that is capable of causing a photochromic material to transform from one form or state to another.

Photochromic materials adapted for use in ophthalmic applications appear to be essentially colorless or "optically clear" when not exposed to actinic radiation (i.e., in the ground-state form) and exhibit a visible color that is characteristic of the absorption spectrum of the activated-state form of the photochromic material upon exposure to actinic radiation. Photochromic compositions and articles that contain one or more photochromic materials, for example photochromic lenses for eyewear applications, may display clear and colored states that generally correspond to the optically clear and colored states of the photochromic material(s) that they contain.

More particularly, for single band absorbing photochromic materials, as specific wavelengths within the visible region of electromagnetic radiation are absorbed by a photochromic material in the activated-state form, the wavelengths within the visible region that are transmitted (i.e., not absorbed) correspond to the color of the photochromic material in the activated-state form. Absorption of light having wavelengths above 500 nm to around 520 nm in the visible region of the electromagnetic spectrum results in a photochromic material that exhibits a "red" or "reddish" color, i.e., it absorbs visible radiation from the short wavelength or "blue end" of the visible spectrum and transmits radiation from the longer wavelength or red end of the visible spectrum. Conversely, absorption of light having wavelengths around 580 nm to around 610 nm in the visible region of the electromagnetic spectrum results in a photochromic material that exhibits a "blue" or "bluish" color, i.e., it absorbs visible radiation from the longer wavelength or "red end" of the visible spectrum and transmits radiation from the shorter wavelength or blue end of the visible spectrum. Photochromics having broadband absorption, that is displaying more than one absorption maximum in the visible region, will tend to exhibit a blended color.

Many current photochromic compounds exhibit red (or reddish) or blue (or bluish) colors. However, for certain applications it may be desirable to have a photochromic material that has a characteristic color other than red or blue. For example, for some ophthalmic applications, it may be desirable to have a photochromic material that has a characteristic green color.

Further, for many applications, it may be desirable that the photochromic material be able to make the transition from the colored activated-state form to the optically clear ground-state form as quickly as possible. For example, in photochromic eyewear applications, ophthalmic lenses comprising photochromic materials may transform from an optically clear state to a colored state as the wearer moves from a region of low actinic radiation, such as indoors, to a region of high actinic radiation, such as into direct sunlight. As the lenses become colored, less electromagnetic radiation having wavelengths within the visible and/or ultraviolet regions of the electromagnetic spectrum is transmitted through the lens to the wearer's eyes. In other words, more electromagnetic radiation is absorbed by the lenses in the colored state than in the optically clear state. When the wearer subsequently moves from the region of high actinic radiation back to a region of low actinic radiation, the photochromic material in the eyewear reverts from the colored, activated-state form to the optically clear, ground-state form in response to thermal energy and the absence of actinic radiation. If, once removed from actinic radiation, the transition from the colored state to the clear state takes several minutes or more, the wearer's vision may be less than optimal during this time due to the combined effects of the lower ambient light and the reduced transmission of visible light through the colored lenses. Accordingly, for certain application, it may be advantageous to develop photochromic materials that may more quickly transition from the optically clear ground state-form to the colored activated-state form and/or transition from the colored activated-state form to the optically clear ground state-form as compared to conventional photochromic materials.

BRIEF SUMMARY OF THE DISCLOSURE

Various non-limiting embodiments of the present invention relate to photochromic materials comprising a metallocenyl group. For example, various non-limiting embodiments disclosed herein provide a photochromic material comprising an indeno-fused naphthopyran and a metallocenyl group bonded to at least one available position on the indeno-fused naphthopyran.

Further non-limiting embodiments disclosed herein provide a photochromic material represented by:

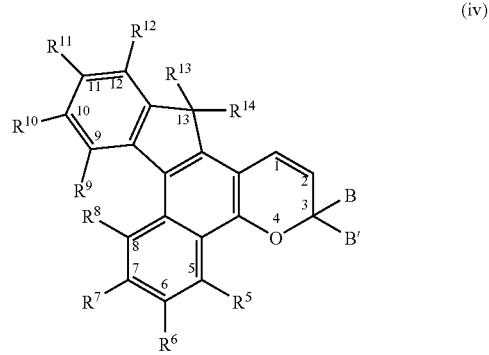

(iv)

wherein:

B and B' are each independently: a metallocenyl group; an aryl group that is mono-substituted with a reactive substituent or a compatiblizing substituent; 9-julolidinyl, an unsubstituted, mono-, di- or tri-substituted aryl group chosen from phenyl and naphthyl, an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, wherein the aryl and heteroaromatic substituents are each independently: hydroxy, aryl, mono- or di-($C_1$-$C_{12}$)alkoxyaryl, mono- or di-($C_1$-$C_{12}$) alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl ($C_1$-$C_{12}$)alkoxy, aryloxy, aryloxy($C_1$-$C_{12}$)alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$) alkoxyaryl($C_1$-$C_{12}$)alkoxy, amino, mono- or di-($C_1$-$C_{12}$) alkylamino, diarylamino, piperazino, N—($C_1$-$C_{12}$) alkylpiperazino, N-arylpiperazino, aziridino, indolino, piperidino, morpholino, thiomorpholino, tetrahydroquinolino, tetrahydroisoquinolino, pyrrolidino, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, halogen or —C(=O)$R^{15}$, wherein $R^{15}$ is —$OR^{16}$, —N($R^{17}$)$R^{18}$, piperidino or morpholino, wherein $R^{16}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl ($C_1$-$C_3$)alkyl, $C_1$-$C_6$ alkoxy($C_2$-$C_4$)alkyl or $C_1$-$C_6$ haloalkyl, and $R^{17}$ and $R^{18}$ are each independently $C_1$-$C_6$ alkyl, $C_5$-$C_7$ cycloalkyl or a substituted or unsubstituted phenyl, wherein said phenyl substituents are each independently $C_1$-$C_6$ alkyl or $C_1$-$C_6$ alkoxy; an unsubstituted or mono-substituted group chosen from pyrazolyl, imidazolyl, pyrazolinyl, imidazolinyl, pyrrolidino, phenothiazinyl, phenoxazinyl, phenazinyl and acridinyl, said substituents being $C_1$-$C_{12}$ alkyl, $C_1$-$C_{12}$ alkoxy, phenyl or halogen; a 4-substituted phenyl, said phenyl substituent being a dicarboxylic acid residue or derivative thereof, a diamine residue or derivative thereof, an amino alcohol residue or derivative thereof, a polyol residue or derivative thereof, —($CH_2$)—, —($CH_2$)$_e$— or —[O—($CH_2$)$_e$]$_f$—, wherein e is an integer ranging from 2 to 6 and f is an integer ranging from 1 to 50, and wherein the substituent is connected to an aryl group on another photochromic material; a group represented by:

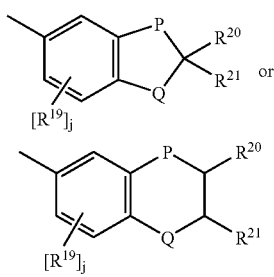

wherein P is —$CH_2$— or —O—; Q is —O— or substituted nitrogen, provided that when Q is substituted nitrogen, P is —$CH_2$—, the substituted nitrogen substituents being hydrogen, $C_1$-$C_{12}$ alkyl or $C_1$-$C_{12}$ acyl; each $R^{19}$ is independently $C_1$-$C_{12}$ alkyl, $C_1$-$C_{12}$ alkoxy, hydroxy or halogen; $R^{20}$ and $R^{21}$ are each independently hydrogen or $C_1$-$C_{12}$ alkyl; and j is an integer ranging from 0 to 2; or a group represented by:

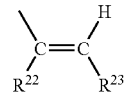

wherein $R^{22}$ is hydrogen or $C_1$-$C_{12}$ alkyl, and $R^{23}$ is an unsubstituted, mono- or di-substituted naphthyl, phenyl, furanyl or thienyl, wherein said naphthyl, phenyl, furanyl and thienyl substituents are each independently $C_1$-$C_{12}$ alkyl, $C_1$-$C_{12}$ alkoxy or halogen; or B and B' taken together form a fluoren-9-ylidene or mono- or di-substituted fluoren-9-ylidene, wherein said fluoren-9-ylidene substituents are each independently $C_1$-$C_{12}$ alkyl, $C_1$-$C_{12}$ alkoxy or halogen;

$R^{13}$ and $R^{14}$ are each independently: a metallocenyl group; a reactive substituent or a compatiblizing substituent; perhalo ($C_1$-$C_{10}$)alkyl, a perhalo($C_2$-$C_{10}$)alkenyl, a perhalo($C_3$-$C_{10}$) alkynyl, a perhalo($C_1$-$C_{10}$)alkoxy or a perhalo($C_3$-$C_{10}$)cycloalkyl; a group represented by —O($CH_2$)$_a$($CX_2$)$_b$$CT_3$, wherein T is a halogen, X is hydrogen or halogen, a is an integer ranging from 1 to 10, and b is an integer ranging from 1 to 10; a silicon-containing group represented by one of

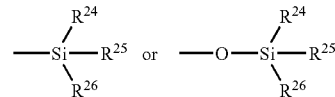

wherein $R^{24}$, $R^{25}$, and $R^{26}$ are each independently $C_1$-$C_{10}$ alkyl, $C_1$-$C_{10}$ alkoxy or phenyl; hydrogen, hydroxy, $C_1$-$C_6$ alkyl, chloro, fluoro, $C_3$-$C_7$ cycloalkyl, allyl or $C_1$-$C_8$ haloalkyl; morpholino, piperidino, pyrrolidino, an unsubstituted, mono- or di-substituted amino, wherein said amino substituents are each independently $C_1$-$C_6$ alkyl, phenyl, benzyl or naphthyl; an unsubstituted, mono-, di- or tri-substituted aryl group chosen from phenyl, naphthyl, benzyl, phenanthryl, pyrenyl, quinolyl, isoquinolyl, benzofuranyl, thienyl, benzothienyl, dibenzofuranyl, dibenzothienyl, carbazolyl or indolyl, wherein the aryl group substituents are each independently halogen, $C_1$-$C_6$ alkyl or $C_1$-$C_6$ alkoxy; —C(=O)$R^{27}$, wherein $R^{27}$ is hydrogen, hydroxy, $C_1$-$C_6$ alkyl, $C_1$-$C_6$ alkoxy, amino, mono- or di-($C_1$-$C_6$)alkylamino, morpholino, piperidino, pyrrolidino, an unsubstituted, mono- or di-substituted phenyl or naphthyl, an unsubstituted, mono- or di-substituted phenoxy, an unsubstituted, mono- or di-substituted phenylamino, wherein said phenyl, naphthyl, phenoxy, and phenylamino substituents are each independently $C_1$-$C_6$ alkyl or $C_1$-$C_6$ alkoxy; —$OR^{28}$, wherein $R^{28}$ is $C_1$-$C_6$ alkyl, phenyl ($C_1$-$C_3$)alkyl, mono($C_1$-$C_6$)alkyl substituted phenyl($C_1$-$C_3$) alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$) alkyl substituted $C_3$-$C_7$ cycloalkyl, $C_1$-$C_8$ chloroalkyl, $C_1$-$C_8$ fluoroalkyl, allyl or $C_1$-$C_6$ acyl, —CH($R^{29}$)$R^{30}$, wherein $R^{29}$ is hydrogen or $C_1$-$C_3$ alkyl, and $R^{30}$ is —CN, —$CF_3$ or —COOR$^{31}$, wherein $R^{31}$ is hydrogen or $C_1$-$C_3$ alkyl, or —C(=O)$R^{32}$, wherein $R^{32}$ is hydrogen, $C_1$-$C_6$ alkyl, $C_1$-$C_6$ alkoxy, amino, mono- or di-($C_1$-$C_6$)alkylamino, an unsubstituted, mono- or di-substituted phenyl or naphthyl, an unsubstituted, mono- or di-substituted phenoxy or an unsubstituted, mono- or di-substituted phenylamino, wherein said phenyl, naphthyl, phenoxy and phenylamino substituents are each independently $C_1$-$C_6$ alkyl or $C_1$-$C_6$ alkoxy; a 4-substituted phenyl, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$— or —[O—(CH$_2$)$_e$]$_f$—, wherein e is an integer ranging from 2 to 6 and f is an integer ranging from 1 to 50, and wherein the substituent is connected to an aryl group on another photochromic material; —CH(R$^{33}$)$_2$, wherein R$^{33}$ is —CN or —COOR$^{34}$, wherein R$^{34}$ is hydrogen, C$_1$-C$_6$ alkyl, C$_3$-C$_7$ cycloalkyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl or an unsubstituted, mono- or di-substituted phenyl or naphthyl, wherein said phenyl and naphthyl substituents are each independently C$_1$-C$_6$ alkyl or C$_1$-C$_6$ alkoxy; —CH(R$^{35}$)R$^{36}$, wherein R$^{35}$ is hydrogen, C$_1$-C$_6$ alkyl or an unsubstituted, mono- or di-substituted phenyl or naphthyl, wherein said phenyl and naphthyl substituents are each independently C$_1$-C$_6$ alkyl or C$_1$-C$_6$ alkoxy, and R$^{36}$ is —C(=O)OR$^{37}$, —C(=O)R$^{38}$ or —CH$_2$OR$^{39}$, wherein R$^{37}$ is hydrogen, C$_1$-C$_6$ alkyl, C$_3$-C$_7$ cycloalkyl, phenyl(C$_1$-C$_3$)alkyl, mono (C$_1$-C$_6$)alkyl substituted phenyl(C$_1$-C$_3$)alkyl, mono(C$_1$-C$_6$) alkoxy substituted phenyl(C$_1$-C$_3$)alkyl or an unsubstituted, mono- or di-substituted phenyl or naphthyl, wherein said phenyl and naphthyl substituents are each independently C$_1$-C$_6$ alkyl or C$_1$-C$_6$ alkoxy, R$^{38}$ is hydrogen, C$_1$-C$_6$ alkyl, amino, mono(C$_1$-C$_6$)alkylamino, di(C$_1$-C$_6$) alkylamino, phenylamino, diphenylamino, (mono- or di-(C$_1$-C$_6$)alkyl substituted phenyl)amino, (mono- or di-(C$_1$-C$_6$)alkoxy substituted phenyl)amino, di(mono- or di-(C$_1$-C$_6$)alkyl substituted phenyl)amino, di(mono- or di-(C$_1$-C$_6$)alkoxy substituted phenyl) amino, morpholino, piperidino or an unsubstituted, mono- or di-substituted phenyl or naphthyl, wherein said phenyl or naphthyl substituents are each independently C$_1$-C$_6$ alkyl or C$_1$-C$_6$ alkoxy, and R$^{39}$ is hydrogen, —C(=O)R$^{37}$, C$_1$-C$_6$ alkyl, C$_1$-C$_3$ alkoxy(C$_1$-C$_6$)alkyl, phenyl(C$_1$-C$_6$)alkyl, monoalkoxy substituted phenyl(C$_1$-C$_6$)alkyl or an unsubstituted, mono- or di-substituted phenyl or naphthyl, wherein said phenyl or naphthyl substituents are each independently C$_1$-C$_6$ alkyl or C$_1$-C$_6$ alkoxy; or R$^{13}$ and R$^{14}$ together form an oxo group, a spiro-carbocyclic group containing 3 to 6 carbon atoms or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings;

R$^5$, R$^8$, R$^9$ and R$^{12}$ are each independently: hydrogen; C$_1$-C$_6$ alkyl; chloro; fluoro; bromo; C$_3$-C$_7$ cycloalkyl; an unsubstituted, mono- or di-substituted phenyl, wherein said phenyl substituents are each independently C$_1$-C$_6$ alkyl or C$_1$-C$_6$ alkoxy; —OR$^{40}$ or —OC(=O)R$^{40}$ wherein R$^{40}$ is hydrogen, amine, alkylene glycol, polyalkylene glycol, C$_1$-C$_6$ alkyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, (C$_1$-C$_6$)alkoxy(C$_2$-C$_4$)alkyl, C$_3$-C$_7$ cycloalkyl, mono(C$_1$-C$_4$)alkyl substituted C$_3$-C$_7$ cycloalkyl or an unsubstituted, mono- or di-substituted phenyl, wherein said phenyl substituents are each independently C$_1$-C$_6$ alkyl or C$_1$-C$_6$ alkoxy; a reactive substituent or a compatiblizing substituent; a 4-substituted phenyl, said phenyl substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$— or —[O—(CH$_2$)$_e$]$_f$—, wherein e is an integer ranging from 2 to 6, and f is an integer ranging from 1 to 50, and wherein the substituent is connected to an aryl group on another photochromic material; —N$^{41}$)R$^{42}$, wherein R$^{41}$ and R$^{42}$ are each independently hydrogen, C$_1$-C$_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, C$_1$-C$_8$ alkylaryl, C$_3$-C$_8$ cycloalkyl, C$_4$-C$_{16}$ bicycloalkyl, C$_5$-C$_{20}$ tricycloalkyl or C$_1$-C$_{20}$ alkoxy(C$_1$-C$_6$)alkyl, or R$^{41}$ and R$^{42}$ come together with the nitrogen atom to form a C$_3$-C$_{20}$ hetero-bicycloalkyl ring or a C$_4$-C$_{20}$ hetero-tricycloalkyl ring; a nitrogen containing ring represented by:

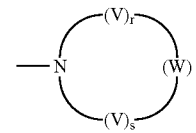

wherein each —V— is independently chosen for each occurrence from —CH$_2$—, —CH(R$^{43}$)—, —C(R$^{43}$)$_2$—, —CH(aryl)-, —C(aryl)$_2$- and —C(R$^{43}$)(aryl)-, wherein each R$^{43}$ is independently C$_1$-C$_6$ alkyl and each aryl is independently phenyl or naphthyl; —W— is —V—, —O—, —S—, —S(O)—, —SO$_2$—, —NH—, —N(R$^{43}$)— or —N(aryl)-; s is an integer ranging from 1 to 3; and r is an integer ranging from 0 to 3, provided that if r is 0 then —W— is the same as —V—; a group represented by:

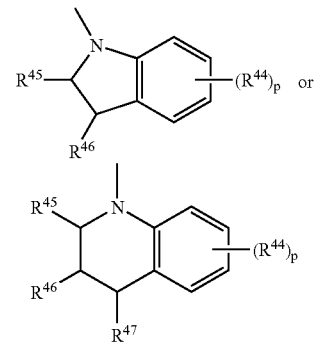

wherein each R$^{44}$ is independently C$_1$-C$_6$ alkyl, C$_1$-C$_6$ alkoxy, fluoro or chloro; R$^{45}$, R$^{46}$ and R$^{47}$ are each independently hydrogen, C$_1$-C$_6$ alkyl, phenyl or naphthyl, or R$^{45}$ and R$^{46}$ together form a ring of 5 to 8 carbon atoms; and p is an integer ranging from 0 to 3; or a substituted or an unsubstituted C$_4$-C$_{18}$ spirobicyclic amine or a substituted or an unsubstituted C$_4$-C$_{18}$ spirotricyclic amine, wherein said substituents are each independently aryl, C$_1$-C$_6$ alkyl, C$_1$-C$_6$ alkoxy or phenyl(C$_1$-C$_6$)alkyl;

R$^7$ and R$^{10}$ are each independently: any of the groups discussed above with respect to R$^5$, R$^8$, R$^9$ and R$^{12}$; or a metallocenyl group;

R$^6$ and R$^{11}$ are each independently: any of the groups discussed above with respect to R$^7$ and R$^{10}$; perfluoroalkyl or perfluoroalkoxy; —C(=O)R$^{48}$ or —SO$_2$R$^{48}$, wherein each R$^{48}$ is independently hydrogen, C$_1$-C$_6$ alkyl, —OR$^{49}$ or —NR$^{50}$R$^{51}$, wherein R$^{49}$, R$^{50}$ and R$^{51}$ are each independently hydrogen, C$_1$-C$_6$ alkyl, C$_5$-C$_7$ cycloalkyl, alkylene glycol, polyalkylene glycol or an unsubstituted, mono- or di-substituted phenyl, wherein said phenyl substituents are each independently C$_1$-C$_6$ alkyl or C$_1$-C$_6$ alkoxy; —C(=C(R$^{52}$)$_2$)R$^{53}$, wherein each R$^{52}$ is independently —C(=O)R$^{48}$, —OR$^{49}$, —OC(=O)R$^{49}$, —NR$^{50}$R$^{51}$, hydrogen, halogen, cyano, C$_1$-C$_6$ alkyl, C$_5$-C$_7$ cycloalkyl, alkylene glycol, polyalkylene glycol or an unsubstituted, mono- or di-substituted phenyl, wherein said phenyl substituents are each independently $C_1$-$C_6$ alkyl or $C_1$-$C_6$ alkoxy, and $R^{53}$ is hydrogen, $C_1$-$C_6$ alkyl, $C_5$-$C_7$ cycloalkyl, alkylene glycol, polyalkylene glycol or an unsubstituted, mono- or di-substituted phenyl, wherein said phenyl substituents are each independently $C_1$-$C_6$ alkyl or $C_1$-$C_6$ alkoxy; or —C≡$R^{54}$ or —C≡N wherein $R^{54}$ is —C(=O)$R^{48}$, hydrogen, $C_1$-$C_6$ alkyl, $C_5$-$C_7$ cycloalkyl or an unsubstituted, mono- or di-substituted phenyl, wherein said phenyl substituents are each independently $C_1$-$C_6$ alkyl or $C_1$-$C_6$ alkoxy; or a least one pair of adjacent groups $R^6$ and $R^7$ or $R^{10}$ and $R^{11}$ together form a group represented by:

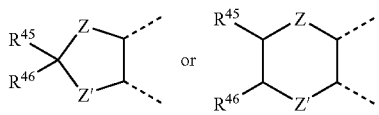

wherein Z and Z' are each independently oxygen or the group —$NR^{41}$—; or $R^6$ and $R^7$ or $R^{10}$ and $R^{11}$ together form an aromatic or heteroaromatic fused group, said fused group being benzo, indeno, dihydronaphthalene, indole, benzofuran, benzopyran or thianaphthene;

provided that the photochromic material comprises at least one metallocenyl group.

Still further non-limiting embodiments provide a photochromic indeno[2',3':3,4]naphtho[1,2-b]pyran comprising a metallocenyl group bonded to at least one of the 3-position, the 6-position, the 7-position, the 10-position, the 11-position or the 13-position of the indeno[2',3':3,4]naphtho[1,2-b]pyran.

Still other non-limiting embodiments of the present invention relate to photochromic compositions, including photochromic coating compositions, and photochromic articles that comprise the photochromic materials according to various non-limiting embodiments disclosed herein and methods of making the same.

BRIEF DESCRIPTION OF THE SEVERAL VIEWS OF THE DRAWINGS

Aspects of the present invention will be better understood when read in conjunction with the figures, in which:

FIGS. 4-6 are general reaction schemes for forming 7H-benzo[C]fluoren-5-ol compounds and indeno-fused naphthopyrans comprising a metallocenyl group that may be useful in forming photochromic materials according to various non-limiting embodiments disclosed herein.

DESCRIPTION OF VARIOUS NON-LIMITING EMBODIMENTS OF THE INVENTION

Figure 1:
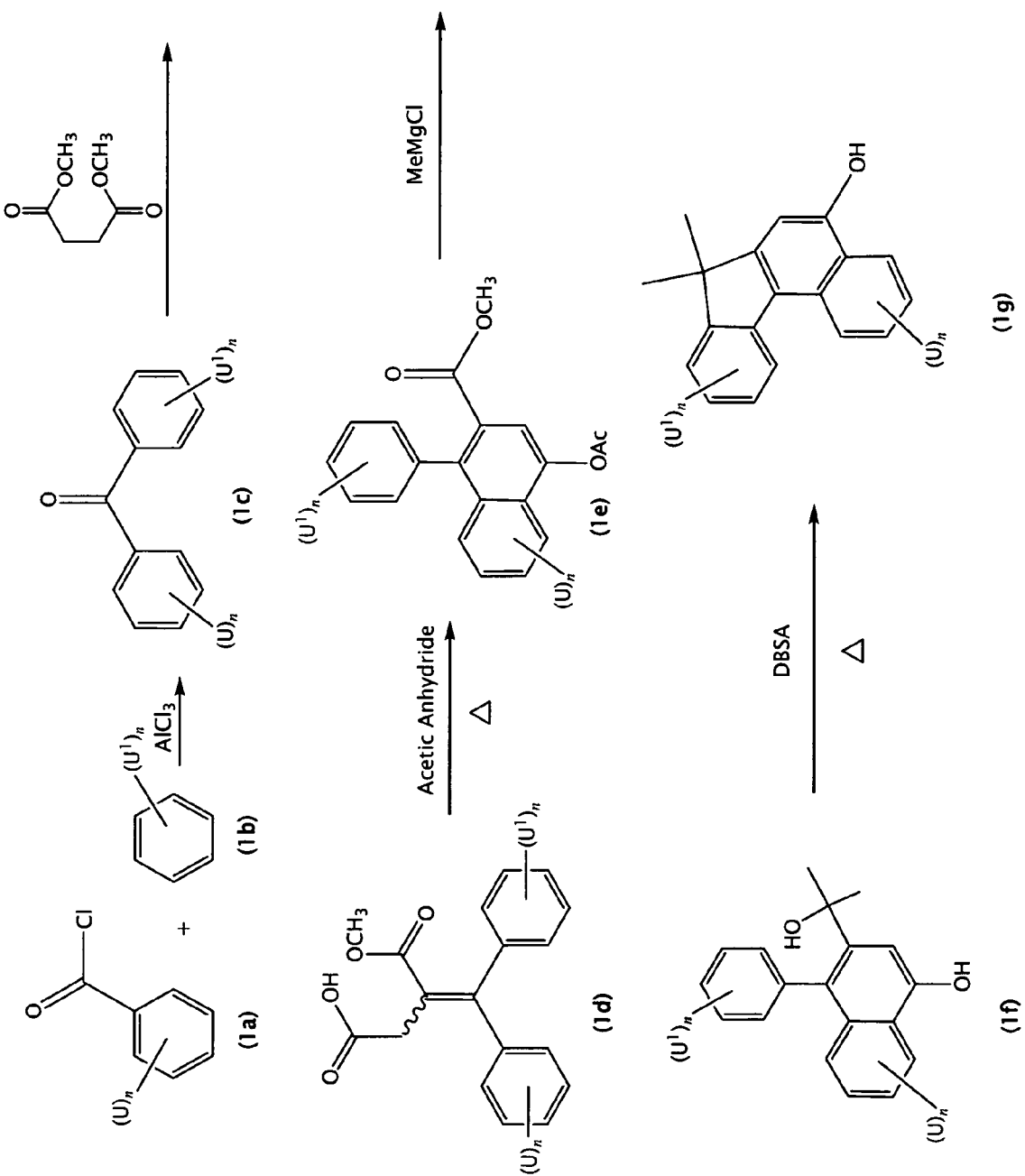
FIG. 1 is a general reaction scheme for forming a 7H-benzo[C]fluoren-5-ol that may be useful in forming photochromic materials according to various non-limiting embodiments disclosed herein.

Various non-limiting embodiments of the present invention will now be described. It is to be understood that while the present invention is described herein in connection with certain embodiments and examples, the present invention is not limited to the particular embodiments and examples disclosed, but is intended to cover modifications that are within the spirit and scope of the invention, as defined by the appended claims. Further, it is to be understood that the present description illustrates aspects of the invention relevant to a clear understanding of the invention. Accordingly, certain aspects of the invention that would be apparent to those of ordinary skill in the art and that, therefore, would not facilitate a better understanding of the invention have not been presented in order to simplify the present description.

As used in this specification and the appended claims, the articles "a," "an," and "the" include plural referents unless expressly and unequivocally limited to one referent. Additionally, for the purposes of this specification, unless otherwise indicated, all numbers expressing quantities, such as weight percentages and processing parameters, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from, for example, the measurement equipment and/or measurement technique. Furthermore, when numerical ranges are set forth herein, these ranges are inclusive of the recited range end point(s).

Moreover, it should be appreciated that where listings of possible substituent groups are provided herein using headings or subheadings, such as, for example: (a), (b) . . . ; (1), (2) . . . ; (i), (ii) . . . ; etc., these headings or subheadings are provided only for convenience of reading and are not intended to limit the choice of substituent groups.

Photochromic materials according to various non-limiting embodiments of the invention will now be discussed. As used herein, the term "photochromic" means having an absorption spectrum for at least visible radiation that varies in response to at least actinic radiation. As used herein, the term "photochromic material" means any substance that is adapted to display photochromic properties, i.e. adapted to have an absorption spectrum for at least visible radiation that varies in response to at least actinic radiation. As discussed above, as used herein, the term "actinic radiation" refers to electromagnetic radiation that is capable of causing a photochromic material to transform from one form or state to another form or state.

Examples of photochromic materials include, without limitation, photochromic groups (e.g., indeno-fused naphthopyrans, etc.), as well as polymers, oligomers, monomers, and other compounds that comprise at least one photochromic group. As used herein, the term "group" means an arrangement of one or more atoms. Further, as used herein, the term "photochromic group" refers to an arrangement of atoms comprising a photochromic moiety. The term "moiety", as used herein, means a part or portion of an organic molecule that has a characteristic chemical property. As used herein, the term "photochromic moiety" refers to the portion of a photochromic group that can undergo reversible transformation from one state to another on exposure to actinic radiation.

The photochromic materials according to various non-limiting embodiments disclosed herein may comprise, in addition to a photochromic group, one or more other groups (e.g., functional groups, aliphatic groups, alicyclic groups, aromatic groups, heteroaromatic groups, heterocyclic groups, etc.) that are linked or fused to the photochromic group or another portion of the photochromic material. As used herein, the term "linked" means covalently bonded. Further, as used herein, the term "fused" means covalently bonded in at least two positions.

Various non-limiting embodiments of the present invention relate to a photochromic material comprising an indeno-fused naphthopyran and a metallocenyl group bonded to at least one available position on the indeno-fused naphthopyran. More particularly, according various non-limiting embodiments of the present invention, the indeno-fused naphthopyran may be a indeno[2',3':3,4]naphtho[1,2-b]pyran. As used herein, the term indeno[2',3':3,4]naphtho[1,2-b]pyran refers to a photochromic group that may be represented by the general structure (i) (below), and which comprises one or more group(s) bonded to the pyran ring at an available position adjacent the oxygen atom (i.e., indicated as the groups B and B' bonded at the 3-position in structure (i) below), which may aid in stabilizing the open-form of the indeno-fused naphthopyran. Non-limiting examples of groups that may be bonded to the pyran ring are described in more detail herein below with reference to the groups B and B'. Further, it will be appreciated by those skilled in the art that any available position in the structure (i) may be substituted or unsubstituted as required. Non-limiting examples of groups that may be bonded to available positions on the indeno[2',3':3,4]naphtho[1,2-b]pyran according to various non-limiting embodiments disclosed herein are set forth herein below in detail.

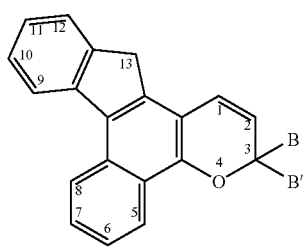

(i)

According to various non-limiting embodiments disclosed herein, the indeno-fused naphthopyran may be an indeno[2',3':3,4]naphtho[1,2-b]pyran and the metallocenyl group may be bonded to the indeno[2',3':3,4]naphtho[1,2-b]pyran at least one of the 3-position, the 6-position, the 7-position, the 10-position, the 11-position or the 13-position thereof. As used herein the term "3-position," "6-position," "7-position," "10-position," "11-position," "13-position," etc. refer to the 3-, 6-, 7-, 10-, 11-, 13-positions, etc. (respectively) of the ring atoms of the indeno-fused naphthopyran as shown by the numbered atoms in structure (i).

As used herein, the term "metallocene group" refers to a group in which two cyclopentadienyl ring ligands form a "sandwich" around a metal ion, wherein each cyclopentadienyl ring is bonded to the metal ion by a pentahapto ($\eta^5$) bonding structure. Metallocene groups have the general empirical formula $(C_5H_5)_2M$, where M is a metal ion having a +2 oxidation state. As used herein, the term "metallocenyl group" refers to a metallocene group that forms or is capable of forming at least one bond with at least one other group, such as, for example, a photochromic group.

Specific non-limiting examples of metallocenyl groups that may be used in connection with the photochromic materials according to various non-limiting embodiments disclosed herein include: ferrocenyl groups, titanocenyl groups, ruthenocenyl groups, osmocenyl groups, vanadocenyl groups, chromocenyl groups, cobaltocenyl groups, nickelocenyl groups, and di-π-cyclopentadienyl-manganese groups. According to one specific non-limiting embodiment, the metallocenyl group that is bonded to the indeno-fused naphthopyran may be a ferrocenyl group.

According to various non-limiting embodiments disclosed herein, the metallocenyl group of the photochromic material may be substituted or unsubstituted. For example, according to various non-limiting embodiments disclosed herein, the metallocenyl group may be represented by one of the following general structures (ii) or (iii) (wherein the dashed line represents an attachment to an indeno-fused naphthopyran, either directly or through a tether, such as, a $C_1$-$C_6$ alkyl, $C_1$-$C_6$ alkoxy, or polyalkylene glycol tether):

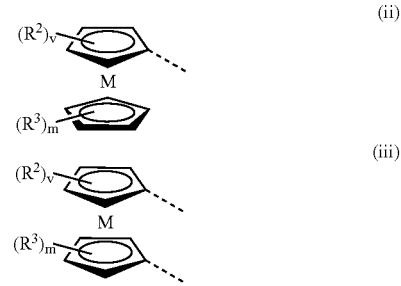

wherein M represent Ti, V, Cr, Mn, Fe, Ru, Os, Co or Ni; v and m each represent an integer from 0 to 3, each $R^2$ independently represents a group, such as, halogen, $C_1$-$C_3$ alkyl, phenyl($C_1$-$C_3$) alkyl, $C_1$-$C_3$ alkoxy, phenyl($C_1$-$C_3$) alkoxy, amino, vinyl or the group —C(O)$R^4$ wherein $R^4$ represents a group, such as, hydrogen, hydroxy, $C_1$-$C_3$ alkyl or phenyl; or two adjacent $R^2$ substituent groups may together form a benzo group; and each $R^3$ may independently represent a group, such as, another photochromic group (for example, another indeno-fused naphthopyran, attached either directly or through a tether, as described above) or any group discussed above with respect to $R^2$. According to certain non-limiting embodiments, M may be Ti, Cr, Fe or Ru.

Figure 7A:
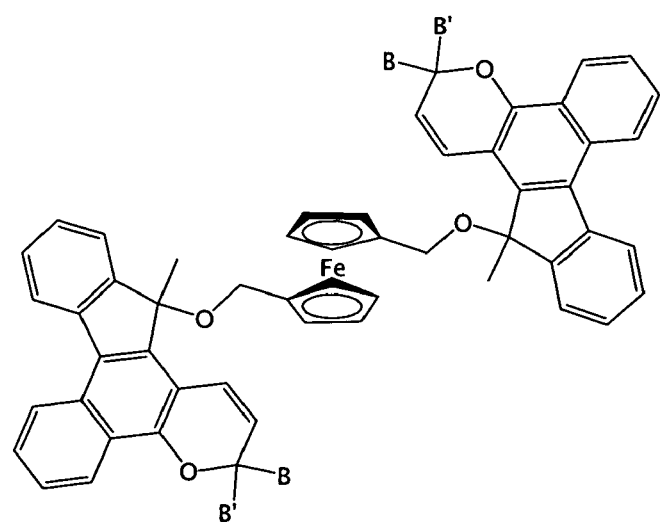
FIGS. 7a-7c are graphic illustrations of photochromic materials according to certain non-limiting embodiments of the present invention.
Figure 7B:
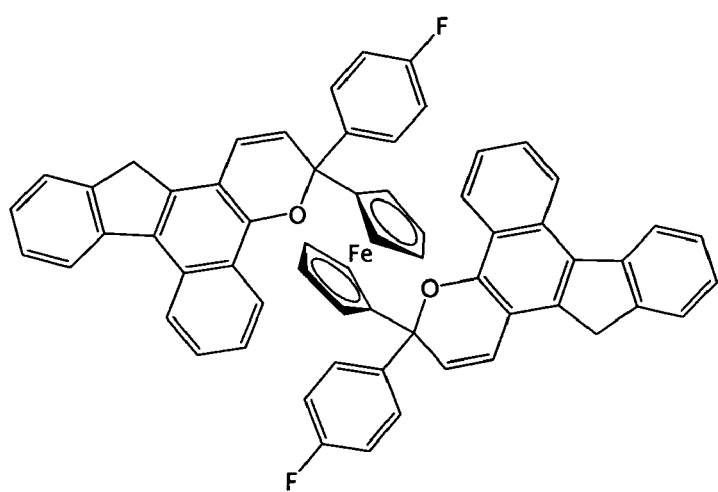
Figure 7C:
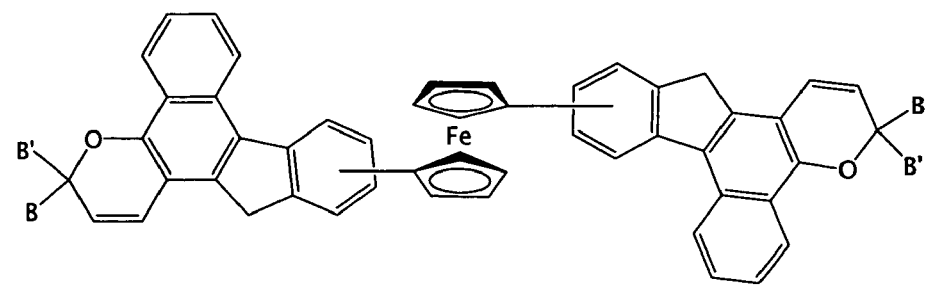

As indicated above, according to certain non-limiting embodiments disclosed herein, $R^3$ may be another photochromic group. That is, according to these non-limiting embodiments, the metallocenyl group can be bonded to two photochromic groups, thereby forming a dimeric photochromic material. The photochromic groups may be attached to the metallocenyl group either directly or via a tether, such as, a $C_1$-$C_6$ alkyl, a $C_1$-$C_6$ alkoxy, or a polyalkylene glycol tether. For example, as illustrated in FIGS. 7a-7c, according to certain non-limiting embodiments of the present disclosure the photochromic material may comprise a metallocenyl group comprising a first and a second cyclopentadienyl ring, wherein the first cyclopentadienyl ring of the metallocenyl group may be bonded, either directly or through a linking chain, to at least one of the 3-position, the 6-position, the 7-position, the 10-position, the 11-position or the 13-position of a first photochromic group (e.g., an indeno[2',3':3,4]naphtho[1,2-b]pyran as shown in FIGS. 7a-7c) and the second cyclopentadienyl ring of the metallocenyl group may be bonded, either directly or through a linking chain, to a corresponding position on another photochromic group (e.g., a second indeno[2',3':3,4]naphtho[1,2-b]pyran as shown in FIGS. 7a-7c).

As discussed above, the photochromic material according to various non-limiting embodiments disclosed herein, may comprise an indeno[2',3':3,4]naphtho[1,2-b]pyran and the metallocenyl group may be bonded to at least one of the 3-position, the 6-position, the 7-position, the 10-position, the 11-position or the 13-position of the indeno[2',3':3,4]naphtho[1,2-b]pyran. According to certain non-limiting embodiments of the present disclosure wherein the photochromic material comprises an indeno[2',3':3,4]naphtho[1,2-b]pyran, the metallocenyl group may be bonded to the indeno[2',3':3,4]naphtho[1,2-b]pyran at the 3-position thereof. Further, according these non-limiting embodiments, the 3-position of the indeno[2',3':3,4]naphtho[1,2-b]pyran may be further substituted with a second group that may be the same as or different from the metallocenyl group. For example, according to these non-limiting embodiments, if the indeno-fused naphthopyran is di-substituted with metallocenyl groups at the 3-position, the metallocenyl groups may be the same or different. Non-limiting examples of groups that, in addition to the metallocenyl group, may be bonded at the 3-position of the indeno[2',3':3,4]naphtho[1,2-b]pyran include:

(a) an aryl group that is mono-substituted with a reactive substituent or a compatiblizing substituent (which are discussed in more detail below);

(b) 9-julolidinyl, an unsubstituted, mono-, di- or tri-substituted aryl group chosen from phenyl and naphthyl, an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, wherein the aryl and heteroaromatic substituents are each independently: hydroxy, aryl, mono- or di-($C_1$-$C_{12}$)alkoxyaryl, mono- or di-($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidino, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, halogen or —C(=O)$R^{15}$, wherein $R^{15}$ represents a group, such as, —O$R^{16}$, —N($R^{17}$)$R^{18}$, piperidino or morpholino, wherein $R^{16}$ represents a group, such as, allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R^{17}$ and $R^{18}$ each independently represents a group, such as, $C_1$-$C_6$ alkyl, $C_5$-$C_7$ cycloalkyl or a substituted or an unsubstituted phenyl, wherein said phenyl substituents are each independently $C_1$-$C_6$ alkyl or $C_1$-$C_6$ alkoxy;

(c) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, said substituents being $C_1$-$C_{12}$ alkyl, $C_1$-$C_{12}$ alkoxy, phenyl or halogen;

(d) a 4-substituted phenyl, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$—, or —[O—(CH$_2$)$_e$]$_f$—, wherein e represents an integer ranging from 2 to 6 and f represents an integer ranging from 1 to 50, and wherein the substituent is connected to an aryl group on another photochromic material;

(e) a group represented by:

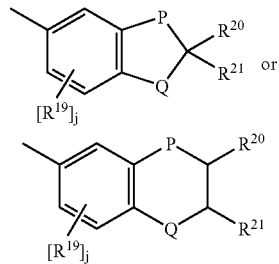

wherein P represents a group, such as, —CH$_2$— or —O—; Q represents a group, such as, —O— or substituted nitrogen, the substituted nitrogen substituents being hydrogen, $C_1$-$C_{12}$ alkyl or $C_1$-$C_{12}$ acyl, provided that if Q represents a substituted nitrogen, P represents —CH$_2$—; each $R^{19}$ independently represents a group, such as, $C_1$-$C_{12}$ alkyl, $C_1$-$C_{12}$ alkoxy, hydroxy or halogen. $R^{20}$ and $R^{21}$ each independently represents a group, such as, hydrogen or $C_1$-$C_{12}$ alkyl; and j represents an integer ranging from 0 to 2; or (f) a group represented by:

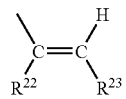

wherein $R^{22}$ represents a group, such as, hydrogen or $C_1$-$C_{12}$ alkyl, and $R^{23}$ represents a group, such as, an unsubstituted, mono- or di-substituted naphthyl, phenyl, furanyl or thienyl, said substituents being $C_1$-$C_{12}$ alkyl, $C_1$-$C_{12}$ alkoxy or halogen.

As indicated above and discuss in more detail herein below, the photochromic materials according to various non-limiting embodiments disclosed herein may comprise a reactive substituent or a compatiblizing substituent. As used herein, the term "reactive substituent" means an arrangement of atoms, wherein a portion of the arrangement comprises a reactive moiety or a residue thereof. As used herein, the term "moiety" means a part or portion of an organic molecule that has a characteristic chemical property. As used herein, the term "reactive moiety" means a part or portion of an organic molecule that may react to form one or more bond(s) with a monomer, an intermediate in a polymerization reaction or with a polymer into which it has been incorporated. As used herein, the term "intermediate in a polymerization reaction" means any combination of two or more monomer units that are capable of reacting to form one or more bond(s) to additional monomer unit(s) to continue a polymerization reaction or, alternatively, reacting with a reactive moiety of the reactive substituent on the photochromic material. For example, although not limiting herein, the reactive moiety may react with an intermediate in a polymerization reaction of a monomer or oligomer as a co-monomer in the polymerization reaction or may react as, for example and without limitation, a nucleophile or electrophile, that adds into the intermediate. Alternatively, the reactive moiety may react with a group (such as, but not limited to a hydroxyl group) on a polymer.

As used herein, the term "residue of a reactive moiety" means that which remains after a reactive moiety has been reacted. For example, the reactive moiety can be reacted with a protecting group, a monomer, a polymer or an intermediate in a polymerization reaction. As used herein, the term "protecting group" means a group that is removably bonded to a reactive moiety that prevents the reactive moiety from participating in a reaction until the group is removed. Optionally, the reactive substituents according to various non-limiting embodiments disclosed herein may further comprise a linking group. As used herein, the term "linking group" means one or more group(s) or chain(s) of atoms that connect the reactive moiety to the photochromic material.

As used herein, the term "compatiblizing substituent" means an arrangement of atoms that can facilitate integration of the photochromic material into another material or solvent. For example, according to various non-limiting embodiments disclosed herein the compatiblizing substituent may facilitate integration of the photochromic material into a hydrophilic material by increasing the miscibility of the photochromic material in water or a hydrophilic polymeric, oligomeric or monomeric material. According to other non-limiting embodiments, the compatiblizing substituent may facilitate integration of the photochromic material into a lipophilic material. Although not limiting herein, photochromic materials according to various non-limiting embodiments disclosed herein that comprise a compatiblizing substituent that facilitates integration into a hydrophilic material may be miscible in hydrophilic material at least to the extent of one gram per liter. Non-limiting examples of compatiblizing substituents include those substituents comprising a group -J, wherein -J represents the group —K (discussed below) or hydrogen.

Further, it should be appreciated that some substituents may be both a compatiblizing substituent and a reactive substituent. For example, a substituent that comprises hydrophilic linking group(s) that connects a reactive moiety to the photochromic material may be both a reactive substituent and a compatiblizing substituent. As used herein, such substituents may be termed as either a reactive substituent or compatiblizing substituent.

Non-limiting examples of reactive and/or compatiblizing substituents that may be used in conjunction with the various non-limiting embodiments disclosed herein may be represented by:

-A-D-E-G-J (v); -G-E-G-J (vi); -D-E-G-J (vii);
-A-D-J (viii); -D-G-J (ix); -D-J (x);
-A-G-J (xi); -G-J (xii); or -A-J (xiii).

With reference to (v)-(xiii) above, non-limiting examples of groups that -A- may represent according to various non-limiting embodiments disclosed herein include —O—, —C(=O)—, —CH$_2$—, —OC(=O)— and —NHC(=O)—, provided that if -A- represents —O—, -A- forms at least one bond with -J.

Non-limiting examples of groups that -D- may represent according to various non-limiting embodiments include: (a) a diamine residue or a derivative thereof, wherein a first amino nitrogen of said diamine residue may form a bond with -A-, or a substituent or an available position on the indeno-fused naphthopyran, and a second amino nitrogen of said diamine residue may form a bond with -E-, -G- or -J; and (b) an amino alcohol residue or a derivative thereof, wherein an amino nitrogen of said amino alcohol residue may form a bond with -A-, or a substituent or an available position on the indeno-fused naphthopyran, and an alcohol oxygen of said amino alcohol residue may form a bond with -E-, -G- or -J. Alternatively, according to various non-limiting embodiments disclosed herein the amino nitrogen of said amino alcohol residue may form a bond with -E-, -G- or -J, and said alcohol oxygen of said amino alcohol residue may form a bond with -A-, or a substituent or an available position on the indeno-fused naphthopyran.

Non-limiting examples of suitable diamine residues that -D- may represent include an aliphatic diamine residue, a cyclo aliphatic diamine residue, a diazacycloalkane residue, an azacyclo aliphatic amine residue, a diazacrown ether residue or an aromatic diamine residue. Specific non-limiting examples of diamine residues that may be used in conjunction with various non-limiting embodiments disclosed herein include the following:

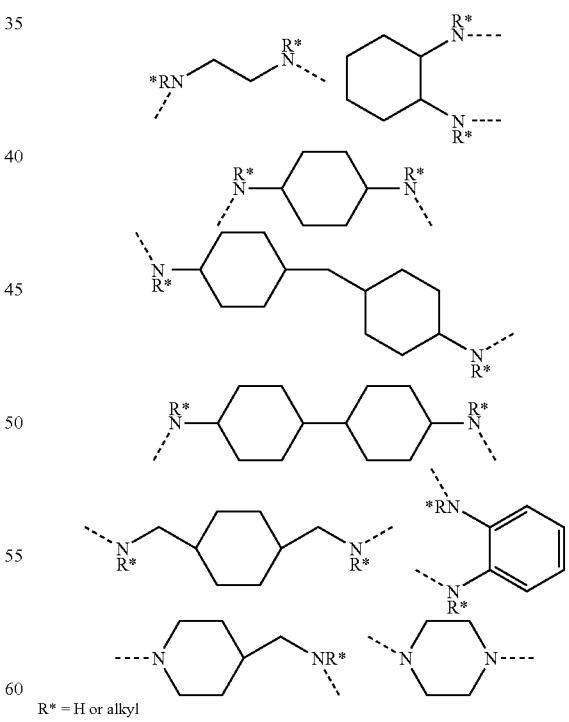

R* = H or alkyl

Non-limiting examples of suitable amino alcohol residues that -D- may represent include an aliphatic amino alcohol residue, a cyclo aliphatic amino alcohol residue, an azacyclo aliphatic alcohol residue, a diazacyclo aliphatic alcohol residue or an aromatic amino alcohol residue. Specific non-limiting examples of amino alcohol residues that may be used in conjunction with various non-limiting embodiments disclosed herein include the following:

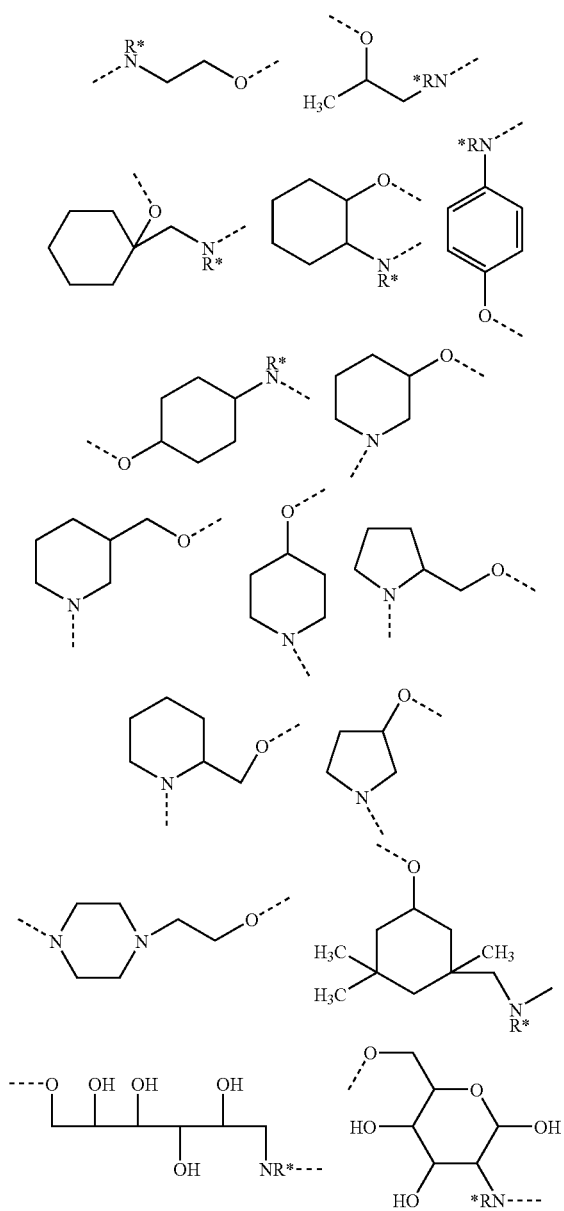

R* = H or alkyl

With continued reference to (v)-(xiii) above, according to various non-limiting embodiments disclosed herein, -E- may represent a dicarboxylic acid residue or a derivative thereof, wherein a first carbonyl group of said dicarboxylic acid residue may form a bond with -G- or -D-, and a second carbonyl group of said dicarboxylic acid residue may form a bond with -G-. Non-limiting examples of suitable dicarboxylic acid residues that -E- may represent include an aliphatic dicarboxylic acid residue, a cycloaliphatic dicarboxylic acid residue or an aromatic dicarboxylic acid residue. Specific non-limiting examples of dicarboxylic acid residues that may be used in conjunction with various non-limiting embodiments disclosed herein include the following:

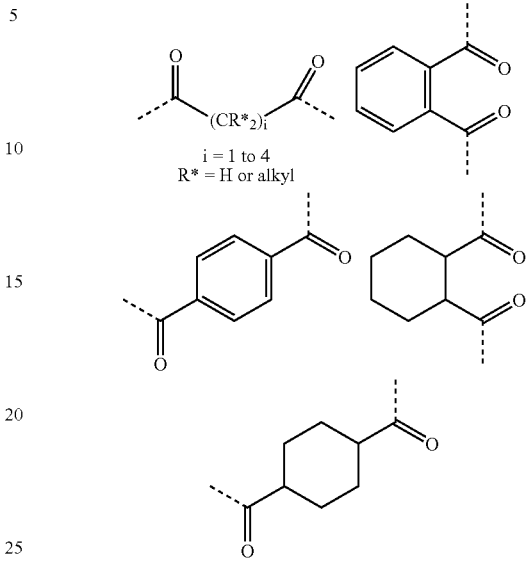

i = 1 to 4
R* = H or alkyl

According to various non-limiting embodiments disclosed herein, -G- may represent: (a) a group —[(OC$_2$H$_4$)$_x$(OC$_3$H$_6$)$_y$(OC$_4$H$_8$)$_z$]—O—, wherein x, y and z are integers that each independently range from 0 to 50, and a sum of x, y, and z ranges from 1 to 50; (b) a polyol residue or a derivative thereof, wherein a first polyol oxygen of said polyol residue may form a bond with -A-, -D-, -E- or a substituent or an available position on the indeno-fused naphthopyran and a second polyol oxygen of said polyol may form a bond with -E- or -J; or (c) a combination of (a) and (b), wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- may represent include an aliphatic polyol residue, a cyclo aliphatic polyol residue or an aromatic polyol residue.

Specific non-limiting examples of polyols from which the polyol residues that -G- may represent may be formed according to various non-limiting embodiments disclosed herein include: (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as, but not limited to, those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to, those set forth in U.S. Pat. No. 6,555,028 at col. 6, lines 13-43, which disclosure is hereby specifically incorporated by reference herein; (h) polyacrylic polyols, such as, but not limited to, those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

Referring again to (v)-(xiii) above, according to various non-limiting embodiments disclosed herein -J may represent a group —K, wherein —K represents a group, such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein w represents an integer ranging from 1 to 18. According to other non-limiting embodiments, -J may represent hydrogen that forms a bond with an oxygen or a nitrogen of linking group to form a reactive moiety, such as —OH or —NH. For example, according to various non-limiting embodiments disclosed herein, -J may represent hydrogen, provided that if -J represents hydrogen, -J is bonded to an oxygen of -D- or -G-, or a nitrogen of -D-.

According to still other non-limiting embodiments, -J may represent a group -L or residue thereof, wherein -L may represent a reactive moiety. For example, according to various non-limiting embodiments disclosed herein, -L may represent a group, such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

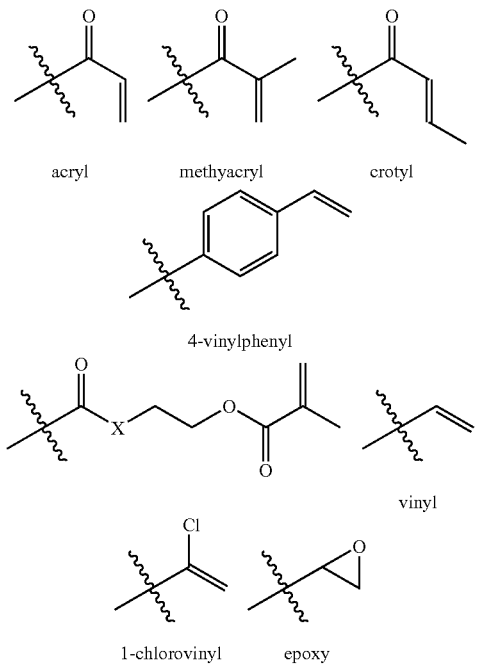

X = NH: 2-(methacryloxy)ethylcarbamyl
X = O: 2-(methacryloxy)ethoxycarbonyl

As previously discussed, -G- may represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue may be formed, for example and without limitation herein, by the reaction of one or more of the polyol hydroxyl groups with a precursor of -A-, such as a carboxylic acid or a methylene halide, a precursor of polyalkoxylated group, such as polyalkylene glycol, or a hydroxyl substituent of the indeno-fused naphthopyran. The polyol may be represented by R'—(OH)$_g$ and the residue of the polyol may be represented by the formula —O—R'—(OH)$_{g-1}$, wherein R' is the backbone or main chain of the polyhydroxy compound and g is at least 2.

Further, as discussed above, one or more of the polyol oxygen atoms of -G- may form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J may be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J may be produced by acidic condensation of one or more of the polyol hydroxyl groups with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. Further, although not limiting herein, if -G- represents a polyol residue and -J represents a group -L chosen from acryl, methacryl, 2-(methacryloxy)ethylcarbamyl and epoxy, -L may be added by condensation of the polyol residue with acryloyl chloride, methacryloyl chloride, 2-isocyanatoethyl methacrylate or epichlorohydrin, respectively.

Further, although not limiting herein, wherein the photochromic material comprises two or more reactive substituents, two or more compatiblizing substituents or a combination of reactive substituents and compatiblizing substituents, each substituent may be the same or different and may be independently chosen from those reactive and/or compatiblizing substituents discussed above. Additional examples of reactive and/or compatiblizing substituents and information regarding methods of forming such substituents on photochromic materials are provided in U.S. patent application Ser. No. 11/102,279 at paragraphs [0051] to [0067]; U.S. patent application Ser. No. 11/102,280, at paragraphs [0017] to [0045]; U.S. Pat. No. 6,555,028, at col. 3, line 45 to col. 4, line 26; and U.S. Pat. No. 6,113,814 at col. 3, lines 30-64, which disclosures are hereby specifically incorporated by reference herein.

Other non-limiting embodiments disclosed herein provide a photochromic material that may be represented by the structure (iv) shown below:

(iv)

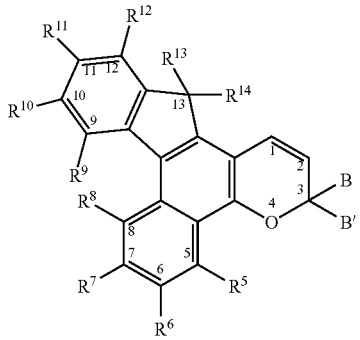

wherein the photochromic material comprises at least one metallocenyl group. For example, according to various non-limiting embodiments disclosed herein, at least one of B, B', $R^6$, $R^7$, $R^{10}$, $R^{11}$, $R^{13}$ and $R^{14}$ (shown above in structure (iv)) may be a metallocenyl group. Suitable non-limiting examples of groups that B, B', and $R^5$-$R^{14}$ may represent according to various non-limiting embodiments disclosed herein are set forth below in more detail.

With continued reference to structure (iv) above, non-limiting examples of groups that B and B' may each independently represent include:

(a) a metallocenyl group (such as those discussed above);

(b) an aryl group that is mono-substituted with a reactive substituent or a compatiblizing substituent (such as those discussed above);

(c) 9-julolidinyl, an unsubstituted, mono-, di- or tri-substituted aryl group chosen from phenyl and naphthyl, an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, wherein the aryl and heteroaromatic substituents are each independently: hydroxy, aryl, mono- or di-($C_1$-$C_{12}$) alkoxyaryl, mono- or di-($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$) alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidino, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, halogen or —C(=O)$R^{15}$, wherein $R^{15}$ is —$OR^{16}$, —N($R^{17}$)$R^{18}$, piperidino or morpholino, wherein $R^{16}$ represents a group, such as, allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R^{17}$ and $R^{18}$ each independently represents a group, such as, $C_1$-$C_6$ alkyl, $C_5$-$C_7$ cycloalkyl or a substituted or an unsubstituted phenyl, wherein said phenyl substituents are each independently $C_1$-$C_6$ alkyl or $C_1$-$C_6$ alkoxy;

(d) an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, said substituents being $C_1$-$C_{12}$ alkyl, $C_1$-$C_{12}$ alkoxy, phenyl or halogen;

(e) a 4-substituted phenyl, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_e$— or —[O—($CH_2$)$_e$]$_f$—, wherein e is an integer ranging from 2 to 6 and f is an integer ranging from 1 to 50, and wherein the substituent is connected to an aryl group on another photochromic material;

(f) a group represented by:

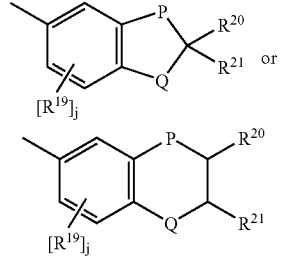

wherein P represents a group, such as, —$CH_2$— or —O—, Q represents a group, such as, —O— or substituted nitrogen, the substituted nitrogen substituents being hydrogen, $C_1$-$C_{12}$ alkyl or $C_1$-$C_{12}$ acyl, provided that when Q is substituted nitrogen, P is —$CH_2$—; each $R^{19}$ independently represents a group, such as, $C_1$-$C_{12}$ alkyl, $C_1$-$C_{12}$ alkoxy, hydroxy or halogen; $R^{20}$ and $R^{21}$ each independently represent a group, such as, hydrogen or $C_1$-$C_{12}$ alkyl; and j represents an integer ranging from 0 to 2; or (g) a group represented by:

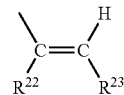

wherein $R^{22}$ represents a group, such as, hydrogen or $C_1$-$C_{12}$ alkyl, and $R^{23}$ represents a group, such as, an unsubstituted, mono- or di-substituted naphthyl, phenyl, furanyl or thienyl, wherein said naphthyl, phenyl, furanyl and thienyl substituents are each independently $C_1$-$C_{12}$ alkyl, $C_1$-$C_{12}$ alkoxy or halogen.

Alternatively, B and B' may represent groups that together form a fluoren-9-ylidene or mono- or di-substituted fluoren-9-ylidene, each of said fluoren-9-ylidene substituents independently being $C_1$-$C_{12}$ alkyl, $C_1$-$C_{12}$ alkoxy or halogen.

Non-limiting examples of groups that $R^{13}$ and $R^{14}$ shown above in structure (iv) may each independently represent include:

(a) a metallocenyl group (such as those discussed above);

(b) a reactive substituent or a compatiblizing substituent (such as those discussed above);

(c) a perhalogenated compound, wherein the perhalogenated compound is at least one of a perhalo($C_1$-$C_{10}$) alkyl, a perhalo($C_2$-$C_{10}$)alkenyl, a perhalo($C_3$-$C_{10}$)alkynyl, a perhalo($C_1$-$C_{10}$)alkoxy or a perhalo($C_3$-$C_{10}$) cycloalkyl;

(d) a group represented by —O(CH$_2$)$_a$(CX$_2$)$_b$CT$_3$, wherein T represents a halogen (e.g., fluorine, chlorine, bromine, etc.), X represents hydrogen or halogen (e.g., fluorine, chlorine, bromine, etc.), a represents an integer ranging from 1 to 10, and b represents an integer ranging from 1 to 10, such as those groups set forth in paragraphs [0019] to [0027] and [0045] to [0068] of U.S. Provisional Patent Application Ser. No. 60/809,732, entitled "Photochromic Materials Comprising Haloalkyl Groups", which was filed on a date even herewith, and which disclosure is hereby specifically incorporated by reference herein;

(e) a silicon-containing group represented by one of

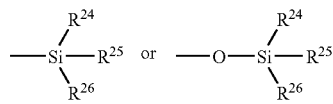

wherein R$^{24}$, R$^{25}$, and R$^{26}$ each independently represents a group, such as, C$_1$-C$_{10}$ alkyl, C$_1$-C$_{10}$ alkoxy or phenyl;

(f) hydrogen, hydroxy, C$_1$-C$_6$ alkyl, chioro, fluoro, C$_3$-C$_7$ cycloalkyl, allyl or C$_1$-C$_8$ haloalkyl;

(g) morpholino, piperidino, pyrrolidino, an unsubstituted, mono- or di- substituted amino, wherein said amino substituents are each independently C$_1$-C$_6$ alkyl, phenyl, benzyl or naphthyl;

(h) an unsubstituted, mono-, di- or tri-substituted aryl group chosen from phenyl, naphthyl, benzyl, phenanthryl, pyrenyl, quinolyl, isoquinolyl, benzofuranyl, thienyl, benzothienyl, dibenzofuranyl, dibenzothienyl, carbazolyl or indolyl, wherein said aryl group substituents are each independently halogen, C$_1$-C$_6$ alkyl or C$_1$-C$_6$ alkoxy;

(i) —C(=O)R$^{27}$, wherein R$^{27}$ represents a group, such as, hydrogen, hydroxy, C$_1$-C$_6$ alkyl, C$_1$-C$_6$ alkoxy, amino, mono- or di-(C$_1$-C$_6$)alkylamino, morpholino, piperidino, pyrrolidino, an unsubstituted, mono- or di-substituted phenyl or naphthyl, an unsubstituted, mono- or di-substituted phenoxy, an unsubstituted, mono- or di-substituted phenylamino, wherein said phenyl, naphthyl, phenoxy, and phenylamino substituents are each independently C$_1$-C$_6$ alkyl or C$_1$-C$_6$ alkoxy;

(j) —OR$^{28}$, wherein R$^{28}$ represents a group, such as: (i) C$_1$-C$_6$ alkyl, phenyl(C$_1$-C$_3$)alkyl, mono(C$_1$-C$_6$)alkyl substituted phenyl(C$_1$-C$_3$)alkyl, mono(C$_1$-C$_6$) alkoxy substituted phenyl(C$_1$-C$_3$)alkyl, C$_1$-C$_6$ alkoxy(C$_2$-C$_4$) alkyl, C$_3$-C$_7$ cycloalkyl, mono(C$_1$-C$_4$)alkyl substituted C$_3$-C$_7$ cycloalkyl, C$_1$-C$_8$ chloroalkyl, C$_1$-C$_8$ fluoroalkyl, allyl or C$_1$-C$_6$ acyl, (ii) —CH(R$^{29}$)R$^{30}$, wherein R$^{29}$ represents a group, such as, hydrogen or C$_1$-C$_3$ alkyl; and R$^{30}$ represents a group, such as, —CN, —CF$_3$ or —COOR$^{31}$, wherein R$^{31}$ represents a group, such as, hydrogen or C$_1$-C$_3$ alkyl, or (iii) —C(=O)R$^{32}$, wherein R$^{32}$ represents a group, such as, hydrogen, C$_1$-C$_6$ alkyl, C$_1$-C$_6$ alkoxy, amino, mono- or di-(C$_1$-C$_6$)alkylamino, an unsubstituted, mono- or di-substituted phenyl or naphthyl, an unsubstituted, mono- or di-substituted phenoxy or an unsubstituted, mono- or di-substituted phenylamino, wherein said phenyl, naphthyl, phenoxy and phenytamino substituents are each independently C$_1$-C$_6$ alkyl or C$_1$-C$_6$ alkoxy;

(k) a 4-substituted phenyl, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$- or —[O—(CH$_2$)$_e$]f-, wherein e represents an integer ranging from 2 to 6 and f represents an integer ranging from 1 to 50, and wherein the substituent is connected to an aryl group of another photochromic material (e.g., an aryl group of an indeno-fused naphthopyran);

(l) —CH(R$^{33}$)$_2$, wherein R$^{33}$ represents a group, such as, —CN or —COOR$^{34}$, wherein R$^{34}$ represents a group, such as, hydrogen, C$_1$-C$_6$ alkyl, C$_3$-C$_7$ cycloalkyl, phenyl(C$_1$-C$_3$)alkyl, mono(C$_1$-C$_6$)alkyl substituted phenyl (C$_1$-C$_3$)alkyl, mono(C$_1$-C$_6$)alkoxy substituted phenyl (C$_1$-C$_3$)alkyl or an unsubstituted, mono- or di-substituted phenyl or naphthyl, wherein said phenyl and naphthyl substituents are each independently C$_1$-C$_6$ alkyl or C$_1$-C$_6$ alkoxy; or (m) —CH(R$^{35}$)R$^{36}$, wherein R$^{35}$ represents a group, such as, hydrogen, C$_1$-C$_6$ alkyl or an unsubstituted, mono- or di-substituted phenyl or naphthyl, wherein said phenyl and naphthyl substituents are each independently C$_1$-C$_6$ alkyl or C$_1$-C$_6$ alkoxy, and R$^{36}$ represents a group, such as, or —C(=O)OR$^{37}$, —C(=O)R$^{38}$ or —CH$_2$OR$^{39}$ wherein:

(i) R$^{37}$ represents a group, such as, hydrogen, C$_1$-C$_6$ alkyl, C$_3$-C$_7$ cycloalkyl, phenyl(C$_1$-C$_3$)alkyl, mono (C$_1$-C$_6$)alkyl substituted phenyl(C$_1$-C$_3$)alkyl, mono (C$_1$-C$_6$)alkoxy substituted phenyl(C$_1$-C$_3$)alkyl or an unsubstituted, mono- or di-substituted phenyl or naphthyl, wherein said phenyl and naphthyl substituents are each independently C$_1$-C$_6$ alkyl or C$_1$-C$_6$ alkoxy, (ii) R$^{38}$ represents a group, such as, hydrogen, C$_1$-C$_6$ alkyl, amino, mono(C$_1$-C$_6$)alkylamino, di(C$_1$-C$_6$) alkylamino, phenylamino, diphenylamino, (mono- or di-(C$_1$-C$_6$)alkyl substituted phenyl)amino, (mono- or di-(C$_1$-C$_6$)alkoxy substituted phenyl)arnino, di(mono- or di-(C$_1$-C$_6$)alkyl substituted phenyl) amino, di(mono- or di-(C$_1$-C$_6$)alkoxy substituted phenyl)amino, morpholino, piperidino or an unsubstituted, mono- or di-substituted phenyl or naphthyl, wherein said phenyl and naphthyl substituents are each independently C$_1$-C$_6$ alkyl or C$_1$-C$_6$ alkoxy, and (iii) R$^{39}$ represents a group, such as, hydrogen, —C(=O)R$^{37}$ (examples of groups that R$^{37}$ may represent are set forth above), C$_1$-C$_6$ alkyl, C$_1$-C$_3$ alkoxy (C$_1$-C$_6$)alkyl, phenyl(C$_1$-C$_6$)alkyl, mono-alkoxy substituted phenyl(C$_1$-C$_6$)alkyl or an unsubstituted, mono- or di-substituted phenyl or naphthyl, wherein said phenyl and naphthyl substituents are each independently C$_1$-C$_6$ alkyl or C$_1$-C$_6$ alkoxy.

Alternatively, R$^{13}$ and R$^{14}$ may each represent groups that together form an oxo group, a spiro-carbocyclic group containing 3 to 6 carbon atoms or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings.

Further, in structure (iv), R$^5$, R$^8$, R$^9$, and R$^{12}$ may each independently represent a group, such as:

(a) hydrogen, C$_1$-C$_6$ alkyl, chloro, fluoro, bromo, C$_3$-C$_7$ cycloalkyl or an unsubstituted, mono- or di-substituted phenyl, wherein said phenyl substituents are each independently C$_1$-C$_6$ alkyl or C$_1$-C$_6$ alkoxy;

(b) —OR$^{40}$ or —OC(=O)R$^{40}$, wherein R$^{40}$ represents a group, such as, hydrogen, amine, alkylene glycol, polyalkylene glycol (e.g., as substituent having the general structure —[O—(C$_t$H$_{2t}$)]$_u$—OR", wherein t and u are each independently integers ranging from 1 to 10, R"

represents a group, such as, hydrogen, alkyl, a reactive substituent or a second photochromic material, non-limiting examples of which may be found in U.S. Pat. No. 6,113,814 at col. 3, lines 30-64, which disclosure is hereby specifically incorporated by reference herein), $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_1$-$C_6$) alkyl, $C_3$-$C_7$ cycloalkyl, mono($C_1$-$C_4$)alkyl substituted $C_3$-$C_7$ cycloalkyl or an unsubstituted, mono- or di-substituted phenyl, wherein said phenyl substituents are each independently $C_1$-$C_6$ alkyl or $C_1$-$C_6$ alkoxy;

(c) a reactive substituent or a compatiblizing substituent;

(d) a 4-substituted phenyl, the substituent being a dicarboxylic acid residue or derivative thereof, a diamine residue or derivative thereof, an amino alcohol residue or derivative thereof, a polyol residue or derivative thereof, —($CH_2$)—, —($CH_2$)$_e$— or —[O—($CH_2$)$_e$]$_f$—, wherein e represents an integer ranging from 2 to 6 and f represents an integer ranging from 1 to 50, and wherein the substituent is connected to an aryl group on another photochromic material (e.g., an aryl group of an indeno-fused naphthopyran);

(e) —N($R^{41}$)$R^{42}$, wherein $R^{41}$ and $R^{42}$ each independently represents a group, such as, hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_8$ alkylaryl, $C_3$-$C_8$ cycloalkyl, $C_4$-$C_{16}$ bicycloalkyl, $C_5$-$C_{20}$ tricycloalkyl or $C_1$-$C_{20}$ alkoxy($C_1$-$C_6$)alkyl, or $R^{41}$ and $R^{42}$ represent groups that come together with the nitrogen atom to form a $C_3$-$C_{20}$ hetero-bicycloalkyl ring or a $C_4$-$C_{20}$ hetero-tricycloalkyl ring;

(f) a nitrogen containing ring represented by:

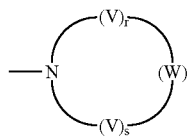

wherein each —V— independently represents a group, such as, —$CH_2$—, —CH($R^{43}$)—, —C($R^{43}$)$_2$—, —CH(aryl)-, —C(aryl)$_2$- and —C($R^{43}$)(aryl)-, wherein each $R^{43}$ independently represents a group, such as, $C_1$-$C_6$ alkyl, and each aryl independently represents a group, such as, phenyl or naphthyl; —W— represents a group, such as, a group that —V— may represent, —O—, —S—, —S(O)—, —$SO_2$—, —NH—, —N($R^{43}$)— or —N(aryl)-; s represents an integer ranging from 1 to 3; and r represents an integer ranging from 0 to 3, provided that if r is 0, then —W— is the same as —V—;

(g) a group represented by:

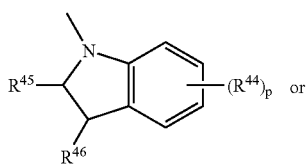

-continued

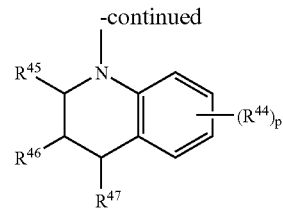

wherein each $R^{44}$ independently represents a group, such as, $C_1$-$C_6$ alkyl, $C_1$-$C_6$ alkoxy, fluoro or chloro; $R^{45}$, $R^{46}$ and $R^{47}$ each independently represents a group, such as, hydrogen, $C_1$-$C_6$ alkyl, phenyl or naphthyl, or $R^{45}$ and $R^{46}$ represents groups that together form a ring of 5 to 8 carbon atoms; and p represents an integer ranging from 0 to 3; or (h) a substituted or an unsubstituted $C_4$-$C_{18}$ spirobicyclic amine or a substituted or an unsubstituted $C_4$-$C_{18}$ spirotricyclic amine, wherein the substituents of the $C_4$-$C_{18}$ spirobicyclic amine or the $C_4$-$C_{18}$ spirotricyclic amine are each independently aryl, $C_1$-$C_6$ alkyl, $C_1$-$C_6$ alkoxy or phenyl($C_1$-$C_6$)alkyl.

Non-limiting examples of groups that $R^7$ and $R^{10}$ (shown above in structure (iv)) may each independently represent include:

(a) any of the groups discussed above with respect to $R^5$, $R^8$, $R^9$ and $R^{12}$; or (b) a metallocenyl group.

Non-limiting examples of groups that $R^6$ and $R^{11}$ in structure (iv) may represent include:

(a) any of the groups discussed above with respect to $R^7$ and $R^{10}$, e.g., any of the groups discussed above with respect to $R^5$, $R^8$, $R^9$, and $R^{12}$ may represent or a metallocenyl group;

(b) perfluoroalkyl or perfluoroalkoxy;

(c) —C(=O)$R^{48}$ or —$SO_2R^{48}$, wherein $R^{48}$ independently represents a group, such as, hydrogen, $C_1$-$C_6$ alkyl, —$OR^{49}$ or —$NR^{50}R^{51}$, wherein $R^{49}$, $R^{50}$ and $R^{51}$ each independently represents a group, such as, hydrogen, $C_1$-$C_6$ alkyl, $C_5$-$C_7$ cycloalkyl, alkylene glycol, polyalkylene glycol (e.g., as substituent having the general structure —[O—($C_tH_{2t}$)]$_u$—OR", wherein t and u are each independently integers ranging from 1 to 10, R" represents a group, such as, hydrogen, alkyl, a reactive substituent or a second photochromic material, non-limiting examples of which may be found in U.S. Pat. No. 6,113,814 at col. 3, lines 30-64, which disclosure is hereby specifically incorporated by reference herein) or an unsubstituted, mono- or di-substituted phenyl, wherein said phenyl substituents are each independently $C_1$-$C_6$ alkyl or $C_1$-$C_6$ alkoxy;

(d) —C(=C($R^{52}$)$_2$)$R^{53}$, wherein each $R^{52}$ independently represents a group, such as, —C(=O)$R^{48}$, —$OR^{49}$, —OC(=O)$R^{49}$, —$NR^{50}R^{51}$, hydrogen, halogen, cyano, $C_1$-$C_6$ alkyl, $C_5$-$C_7$ cycloalkyl, alkylene glycol, polyalkylene glycol (e.g., as substituent having the general structure —[O—($C_tH_{2t}$)]$_u$—OR", as discussed above) or an unsubstituted, mono- or di-substituted phenyl, wherein said phenyl substituents are each independently $C_1$-$C_6$ alkyl or $C_1$-$C_6$ alkoxy, and $R^{53}$ represents a group, such as, hydrogen, $C_1$-$C_6$ alkyl, $C_5$-$C_7$ cycloalkyl, alkylene glycol, polyalkylene glycol or an unsubstituted, mono- or di-substituted phenyl, wherein said phenyl substituents are each independently $C_1$-$C_6$ alkyl or $C_1$-$C_6$ alkoxy; or (e) —C≡CR$^{54}$ or —C≡N, wherein R$^{54}$ represents a group, such as, —C(=O)R$^{48}$, hydrogen, C$_1$-C$_6$ alkyl, C$_5$-C$_7$ cycloalkyl or an unsubstituted, mono- or di-substituted phenyl, wherein said phenyl substituents are each independently C$_1$-C$_6$ alkyl or C$_1$-C$_6$ alkoxy.

Alternatively, according to various non-limiting embodiments disclosed herein wherein the photochromic material may be represented by structure (iv) above, adjacent groups represented by R$^6$ and R$^7$ and/or adjacent groups represented by R$^{10}$ and R$^{11}$ may together form a group represented by:

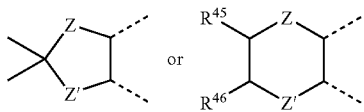

wherein Z and Z' may each independently represent oxygen or the group —NR$^{41}$—, wherein R$^{41}$, R$^{45}$ and R$^{46}$ each represents a group such as those set forth above; or adjacent groups (e.g., R$^6$ and R$^7$ and/or R$^{10}$ and R$^{11}$) may together form an aromatic or heteroaromatic fused group, said fused group being benzo, indeno, dihydronaphthalene, indole, benzofuran, benzopyran or thianaphthene. For example, according to one non-limiting embodiment, R$^6$ and R$^7$ may come together to form a five- or six-membered dioxo ring (i.e., Z and Z' are both oxygen) wherein R$^{45}$ and R$^{46}$ may each independently represent hydrogen, C$_1$-C$_6$ alkyl, phenyl or naphthyl, or R$^{45}$ and R$^{46}$ may represent groups that together form a ring of 5 to 8 carbon atoms. According to one specific non-limiting embodiment, R$^6$ and R$^7$ come together to form a five- or six-membered dioxo ring wherein R$^{45}$ and R$^{46}$ are each hydrogen or C$_1$-C$_6$ alkyl.

Specific non-limiting examples of photochromic materials according to various non-limiting embodiments disclosed herein, wherein the photochromic material is represented by structure (iv) above and comprises a metallocenyl group, include: 3-phenyl-3-ferrocenyl-13,13-dimethyl-3H,13H-indeno[2',3':3,4]naphtho[1,2-b]pyran; 3-(4-fluorophenyl)-3-ferrocenyl-13,13-dimethyl-3H,13H-indeno[2',3':3,4]naphtho[1,2-b]pyran; 3-(4-fluorophenyl)-3-ferrocenyl-6,7-dimethoxy-13,13-dimethyl-3H,13H-indeno[2',3':3,4]naphtho[1,2-b]pyran; 3-(4-fluorophenyl)-3-ferrocenyl-6,7-dimethoxy-13-ethyl-13-hydroxy-3H,13H-indeno[2',3':3,4]naphtho[1,2-b]pyran; 3-(4-fluorophenyl)-3-ferrocenyl-6-morpholino-7-methoxy-13-ethyl-13-hydroxy-3H,13H-indeno[2',3':3,4]naphtho[1,2-b]pyran; and 3-(4-fluorophenyl)-3-ferrocenyl-6,7-dimethoxy-11-phenyl-13,13-dimethyl-3H,13H-indeno[2',3':3,4]naphtho[1,2-b]pyran.

As previously discussed, photochromic materials are materials that are adapted to display photochromic properties, that is, they are adapted to have an absorption spectrum for at least visible radiation that varies in response to at least actinic radiation. Generally speaking, a photochromic material will have a first absorption spectrum associated with its ground-state form and a second absorption spectrum associated with its activated-state form, that is, the form of the photochromic material on exposure to actinic radiation. For single-band absorbing photochromic materials, if the activated-state form of the photochromic material absorbs a substantial portion of visible radiation having wavelengths between 580 nm and 610 nm, the photochromic material will tend to display a blue or bluish-color (i.e., a somewhat blue color or color in the blue family). Alternatively, if the photochromic material in its activated-state form absorbs a substantial portion of visible radiation having wavelengths above 500 nm to 520 nm, the photochromic material will tend to display a red or reddish-color (i.e., a somewhat red color or color in the red family).

However, as previously discussed, for certain applications, such as lenses for eyewear applications, photochromic materials that exhibit a color other than red or blue may be desirable. The photochromic materials according to various non-limiting embodiments disclosed herein comprising a metallocenyl, such as, a ferrocenyl group, for example, a photochromic material comprising a indeno[2',3':3,4]naphtho[1,2-b]pyran and a ferrocenyl group bonded to the 3-position of the indeno[2',3':3,4]naphtho[1,2-b]pyran, may display a green or greenish-color (i.e., a somewhat green color or color in the green family), when exposed to actinic radiation (that is, when the photochromic material is in its activated-state/"open" form).

Further, the photochromic materials comprising an indeno-fused naphthopyran and a metallocenyl, such as, a ferrocenyl group, for example a ferrocenyl group bonded to the 3-position of the indeno-fused naphthopyran, according to various non-limiting embodiments disclosed herein may have faster fade rates (i.e., smaller T$_{1/2}$ values) as compared to a comparable indeno-fused naphthopyran without the metallocenyl group. That is, as compared to an indeno-fused naphthopyran with a comparable structure except for replacing the ferrocenyl group with another group, such as, for example, a 4-phenylmorpholino group, the photochromic material comprising the ferrocenyl group may require less time to transition from its activated-state form to its ground state-form. As previously discussed, for certain applications, such as lenses for eyewear applications, photochromic materials having faster fade rates may be desirable.

Figure 2:
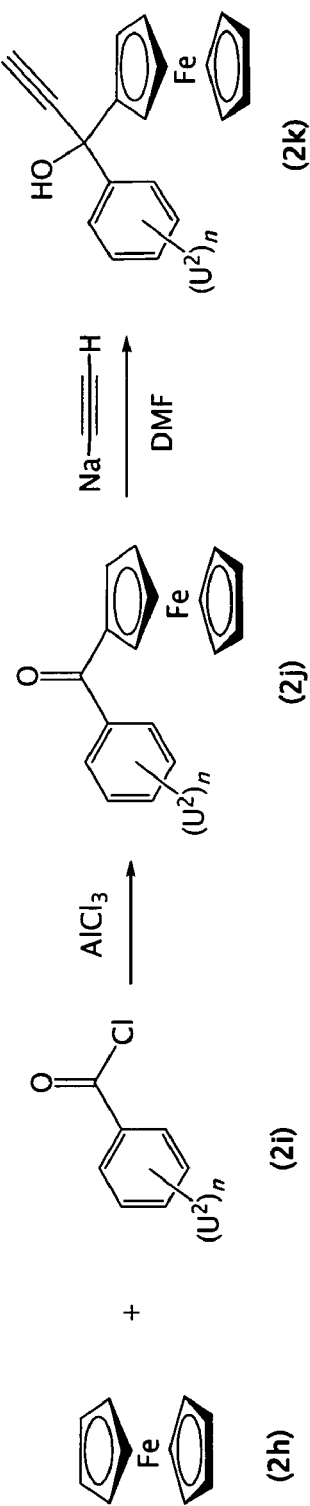
FIG. 2 is a general reaction scheme for forming a substituted 2-propyn-1-ol comprising a metallocenyl group that may be useful in forming photochromic materials according to various non-limiting embodiments disclosed herein.
Figure 3:
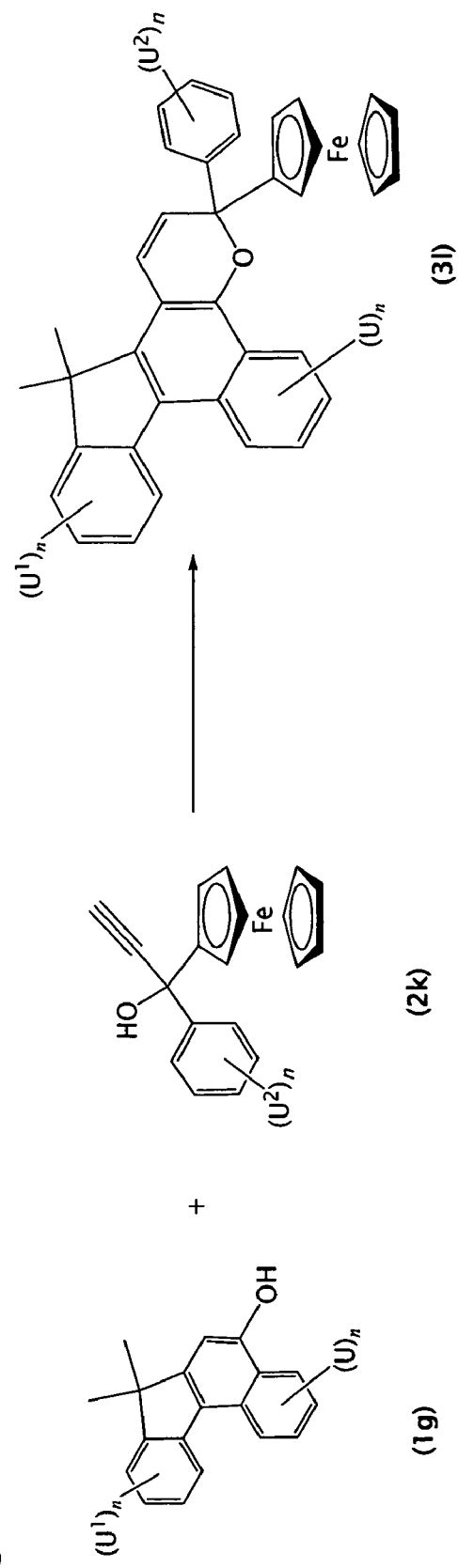
FIG. 3 is a general reaction scheme for forming a photochromic material comprising a metallocenyl group according to various non-limiting embodiments disclosed herein.

Methods of making photochromic materials according to various non-limiting embodiments will now be described with reference to FIGS. 1-6. FIGS. 1, 4, 5 and 6 depict generalized reaction schemes for making 7H-benzo[C]fluoren-5-ol compounds that may be further reacted with a substituted 2-propyn-1-ol to form photochromic materials comprising a metallocenyl group according to various non-limiting embodiments disclosed herein. FIG. 2 depicts a generalized reaction scheme for forming a substituted 2-propyn-1-ol comprising a metallocenyl group that may be used in forming photochromic materials according to various non-limiting embodiments disclosed herein. FIG. 3 depicts a generalized reaction scheme for forming a photochromic material using a substituted 2-propyn-1-ol comprising a metallocenyl group, which may be formed as depicted in FIG. 2, and a 7H-benzo[C]fluoren-5-ol, which may be formed as depicted in FIGS. 1 and 4-6. In view of the present disclosure and examples, those skilled in the art will recognize modifications to these reaction schemes, as well as other reaction schemes not presented herein, that may be used to form photochromic material according to the present invention. Accordingly, it should be appreciated that these reaction schemes, as well as the specific working examples set forth below in the Example section, are presented for illustration purposes only and are not intended to in any way limit the invention as set forth in the claims.

Referring now to FIG. 1, a solution of a benzoyl chloride, represented by structure (1a) in FIG. 1, which may have one or more substituents U (where n is an integer ranging from 0 to 4), and benzene, represented by structure (1b) in FIG. 1, which may have one or more substituents U$^1$ (where n is an integer ranging from 0 to 4), in methylene chloride are added to a reaction flask. Non-limiting examples of groups that U may represent include those groups discussed above with respect to $R^5$-$R^8$. Non-limiting examples of groups that $U^1$ may represent include those groups discussed above with respect to $R^9$-$R^{12}$. Anhydrous aluminum chloride may be used to catalyze a Friedel-Crafts acylation to give a substituted benzophenone represented by structure (1c) in FIG. 1. This material may then be reacted in a Stobbe reaction with dimethyl succinate to produce a mixture of half-acids, half-esters, which mixture is generally represented by structure (1d) in FIG. 1. Thereafter, the mixture of half acids, half-esters may be reacted with acetic anhydride in toluene at an elevated temperature to produce, after recrystallization, a mixture of substituted naphthalene compounds, one of which is generally represented by structure (1e) in FIG. 1. The mixture of substituted naphthalene compounds may then be reacted with methyl magnesium chloride to produce a mixture of substituted naphthalene compounds, one of which is generally represented by structure (1f) in FIG. 1. The mixture of substituted naphthalene compounds may then be cyclized with acid, for example, dodecylbenzene sulfonic acid ("DBSA") to give a mixture of 7H-benzo[C]fluoren-5-ol compounds, one of which is generally represented by structure (1 g) in FIG. 1. The mixtures may be separated by conventional means at any convenient point during the synthesis depicted in FIG. 1. Other non-limiting methods of forming 7H-benzo[C]fluoren-5-ol compounds that may be useful in forming photochromic material according to various non-limiting embodiments disclosed herein are described in U.S. Pat. No. 6,296,785 at col. 16, lines 1 to 15 (Reaction F), and col. 21, line 29 to col. 23, line 14 (Reaction K), which disclosure is hereby specifically incorporated by reference herein. Methods of forming hydroxy-substituted 7H-benzo [C]fluorenone compounds, which may be further reacted (for example, as shown in U.S. Pat. No. 6,296,785 at col. 13, line 22 to col. 14, line 48, Reactions D and E, which disclosure is hereby specifically incorporated by reference herein) using an appropriate substituted 2-propyn-1-ol (as discussed below) to form photochromic materials according to various non-limiting embodiments disclosed herein, are described in U.S. Pat. No. 6,296,785 at col. 10, line 52 to col. 13, line 22, and col. 19, line 16 to col. 21, line 28 (Reaction J), which disclosure is hereby specifically incorporated by reference herein.

Referring now to FIG. 2, a substituted 2-propyn-1-ol comprising a metallocenyl group, and particularly a ferrocenyl group as shown in FIG. 2, may be prepared as shown. More particularly in FIG. 2, ferrocene (2h) may be reacted with a benzoyl chloride, represented by structure (2i), which may have one or more substituents $U^2$, to form the compound represented by structure (2j) in FIG. 2. Non-limiting examples of groups that $U^2$ may represent include for example, those aryl substituents discussed above with respect to the groups B or B'. A solution of the compound represented by structure (2j) in dimethyl formamide may be reacted with sodium acetylide to form a substituted 2-propyn-1-ol comprising a ferrocenyl group as represented by structure (2k) in FIG. 2. The substituted 2-propyn-1-ol may then be further reacted with the above-described 7H-benzo[C]fluoren-5-ol compounds as shown in FIG. 3 to form an indeno-fused naphthopyran having a metallocenyl substituent according to certain non-limiting embodiments of the present disclosure.

For example, referring now to FIG. 3, the 7H-benzo[C] fluoren-5-ol compounds represented by structure (1g) may be further reacted with the ferrocenyl-substituted 2-propyn-1-ol represented by structure (2k) to produce the indeno-fused naphthopyran (represented by structure (3l) in FIG. 3) according to certain non-limiting embodiments disclosed herein.

Referring now to FIGS. 4-6, there are shown additional generalized reaction schemes for forming metallocenyl substituted indeno-fused naphthopyrans and metallocenyl-substituted 7H-benzo[C]fluoren-5-ol compounds that may be used to form photochromic materials comprising an indeno-fused naphthopyran and a metallocenyl group bonded to the indeno-fused naphthopyran according to various non-limiting embodiments of the present invention. For example, as shown in FIG. 4, the 7,7-dimethyl-7H-benzo[C]fluoren-5-ol compound comprising at least one bromo group represented by $Y^1$ and/or $Y^2$ as shown in structure (4m) and ferroceneboronic acid, represented by structure (4n), may be reacted in water/ethylene glycol dimethyl ether solution using a catalyst (such as tetrakis(triphenylphosphine)palladium) and a base (such as sodium carbonate) to form the ferrocenyl-substituted 7H-benzo[C]fluoren-5-ol compound represented by structure (4o). For clarity, the ferrocenyl substituent(s) are represented by "Fc" in FIGS. 4 and 5. The ferrocenyl-substituted 7H-benzo[C]fluoren-5-ol, represented by structure (4o) compound may comprise one ferrocenyl group, or alternatively, it may comprise more than one ferrocenyl group, for example, when $Y^1$ and $Y^2$ in (4m) are both bromo. Thereafter, the ferrocenyl-substituted 7H-benzo[C]fluoren-5-ol compound may be further reacted with a suitable substituted 2-propyn-1-ol, which may or may not comprise an additional ferrocenyl group, to form an indeno-fused naphthopyran comprising at least one ferrocenyl group bonded thereto according to various non-limiting embodiments of the present invention.

Alternatively, as shown in FIG. 5, the indeno-fused naphthopyran compound comprising at least one hydroxyl group represented by $Y^3$ or $Y^4$ as shown in structure (5p) may be reacted with 1-ferrocenylmethylbromide, which is represented by structure (5q) to form the ferrocenylmethoxy-substituted indeno-fused naphthopyran represented by structure (5r), that is, an indeno-fused naphthopyran comprising at least one ferrocenyl group bonded thereto according to various non-limiting embodiments of the present invention. The ferrocenylmethoxy-substituted indeno-fused naphthopyran, represented by structure (5r), may comprise one ferrocenylmethoxy group or, alternatively, it may comprise more than one ferrocenyl group, for example, when $Y^3$ and $Y^4$ in (5p) both comprise hydroxy groups.

As shown in FIG. 6, the indeno-fused naphthopyran having a hydroxyl group in the 13-position, which may additionally comprise groups represented by $Y^5$ or $Y^6$ (wherein n is an integer ranging from 0 to 4 and $Y^5$ and $Y^6$ may represent groups as discussed above for $U^1$ and U, respectively) as shown in structure (6s), may be reacted with ferrocenyl-methanol, represented by structure (6t), to form the 13-ferrocenylmethoxy-indeno-fused naphthopyran compound represented by structure (6u), that is, an indeno-fused naphthopyran comprising at least one ferrocenyl group bonded thereto according to various non-limiting embodiments of the present invention.

One skilled in the art will recognize that various changes or modifications may be made to the synthesis procedures described above and illustrated in FIGS. 1-6 without deviating from the scope and nature of the invention as described herein and set forth in the claims. As indicated above, these reaction schemes are presented for illustration only and are not intended to be limiting herein.

As discussed above, the photochromic materials according to various non-limiting embodiments disclosed herein may be incorporated into at least a portion of an organic material, such as a polymeric, oligomeric or monomeric material to form a photochromic composition, which photochromic composition may be used, for example and without limitation, to form photochromic articles, such as optical elements, and coating compositions that may be applied to various substrates. As used herein, the terms "polymer" and "polymeric material" refer to homopolymers and copolymers (e.g., random copolymers, block copolymers, and alternating copolymers), as well as blends and other combinations thereof. As used herein, the terms "oligomer" and "oligomeric material" refer to a combination of two or more monomer units that are capable of reacting with additional monomer unit(s). As used herein, the term "incorporated into" means physically and/or chemically combined with. For example, the photochromic materials according to various non-limiting embodiments disclosed herein may be physically combined with at least a portion of an organic material, for example and without limitation, by mixing or imbibing the photochromic material into the organic material; and/or chemically combined with at least a portion of an organic material, for example and without limitation, by copolymerization or otherwise bonding the photochromic material to the organic material.

Further, it is contemplated that the photochromic materials according to various non-limiting embodiments disclosed herein may each be used alone in the photochromic compositions and articles disclosed herein, or may be used in combination with other photochromic materials according to various non-limiting embodiments disclosed herein, or in combination with an appropriate complementary conventional photochromic material. For example, the photochromic materials according to various non-limiting embodiments disclosed herein may be used in conjunction with conventional photochromic materials having activated-state form absorption maxima within the range of 300 to 1000 nanometers, such as, for example, within the range of 400 to 800 nanometers. Further, the photochromic materials according to various non-limiting embodiments disclosed herein may be used in conjunction with a complementary conventional polymerizable or a compatiblized photochromic material, such as for example, those disclosed in U.S. Pat. Nos. 6,113,814 (at col. 2, line 39 to col. 8, line 41) and 6,555,028 (at col. 2, line 65 to col. 12, line 56), which disclosures are hereby specifically incorporated by reference herein.

As discussed above, according to various non-limiting embodiments disclosed herein, the photochromic compositions (as well as the photochromic articles discussed herein) may contain a mixture of photochromic materials. For example, although not limiting herein, mixtures of photochromic materials may be used to attain certain activated colors, such as a near neutral gray or near neutral brown. For example, U.S. Pat. No. 5,645,767, col. 12, line 66 to col. 13, line 19, describes the parameters that define neutral gray and brown colors and which disclosure is specifically incorporated by reference herein.

Various non-limiting embodiments disclosed herein provide a photochromic composition comprising an organic material, the organic material being at least one of a polymeric material, an oligomeric material and a monomeric material, and a photochromic material according to any of the non-limiting embodiments set forth above incorporated into at least a portion of the organic material. According to various non-limiting embodiments disclosed herein, the photochromic material may be incorporated into a portion of the organic material by blending and/or bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof. For example, although not limiting herein, the photochromic material may be linked to the organic material through a reactive substituent, such as those as discussed above.

According to one non-limiting embodiment wherein the organic material is a polymeric material, the photochromic material may be incorporated into at least a portion of the polymeric material or at least a portion of a monomeric material or oligomeric material from which the polymeric material is formed. For example according to various non-limiting embodiments disclosed herein, photochromic materials that have a reactive substituent may be bonded to an organic material, such as a monomer, oligomer or polymer, having a group with which a reactive moiety of the reactive substituent may be reacted, or the reactive moiety may be reacted as a co-monomer in the polymerization reaction from which the organic material is formed, for example, in a co-polymerization process.

As discussed above, the photochromic compositions according to various non-limiting embodiments disclosed herein may comprise an organic material chosen from a polymeric material, an oligomeric material and/or a monomeric material. Examples of polymeric materials that may be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene)-dimethacrylate; poly(alkoxylated phenol methacrylates); cellulose acetate; cellulose triacetate; cellulose acetate propionate; cellulose acetate butyrate; poly(vinyl acetate); poly (vinyl alcohol); poly(vinyl chloride); poly(vinylidene chloride); polyurethanes; polythiourethanes; thermoplastic polycarbonates; polyesters; poly(ethylene terephthalate); polystyrene; poly($\alpha$-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate and butyl acrylate. Also contemplated are copolymers of the aforementioned monomers, combinations, and blends of the aforementioned polymers and copolymers with other polymers, e.g., to form interpenetrating network products.

Further, according to various non-limiting embodiments wherein transparency of the photochromic composition is desired, the organic material may be a transparent polymeric material. For example, according to various non-limiting embodiments, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to certain non-limiting embodiments, the polymeric material may be an optical resins sold by PPG Industries, Inc. under the CR-designation, e.g., CR-307, CR-407, and CR-607.

According to certain non-limiting embodiments, the organic material may be a polymeric material chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

Further, it will be appreciated by those skilled in the art that the photochromic compositions according to various non-limiting embodiments disclosed herein may further comprise other additives that aid in the processing and/or performance of the composition or a coating or article derived therefrom. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as, hexanediol diacrylate and coupling agents), and combinations and mixtures thereof.

As previously discussed, the present invention further contemplates photochromic articles, such as optical elements, made using the photochromic materials and/or the photochromic compositions according to various non-limiting embodiments disclosed herein. As used herein, the term "optical" means pertaining to or associated with light and/or vision. The optical elements according to various non-limiting embodiments disclosed herein may include, without limitation, ophthalmic elements, display elements, windows, mirrors, and liquid crystal cell elements. As used herein, the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect or enhance (cosmetically or otherwise) vision, including without limitation, contact lenses and other intraocular elements, magnifying lenses, protective lenses, visors, goggles, as well as, lenses for optical instruments (for example, cameras and telescopes). As used herein, the term "display" means the visible or machine-readable representation of information in words, numbers, symbols, designs or drawings. Non-limiting examples of display elements include screens, monitors, and security elements, such as security marks. As used herein, the term "window" means an aperture adapted to permit the transmission of radiation therethrough. Non-limiting examples of windows include automotive and aircraft transparencies, windshields, filters, shutters, and optical switches. As used herein, the term "mirror" means a surface that specularly reflects a large fraction of incident light. As used herein, the term "liquid crystal cell" refers to a structure containing a liquid crystal material that is capable of being ordered. One non-limiting example of a liquid crystal cell element is a liquid crystal display.

Various non-limiting embodiments disclosed herein provide photochromic articles, such as optical elements, comprising a substrate and a photochromic material according to any of the non-limiting embodiments discussed above connected to a portion of the substrate. As used herein, the term "connected to" means associated with, either directly or indirectly through another material or structure. Further, as used herein in the context of a coating being "on" a surface or object, the term "on" means that the subject coating is connected to the surface or object such that the subject coating is supported or carried by the surface or object. For example, a coating that is "on" a surface may be applied directly over the surface or it may be applied over one or more other coatings, at least one of which is applied directly over the surface.

According to various non-limiting embodiments disclosed herein wherein the substrate of the photochromic article comprises a polymeric material, the photochromic material may be connected to at least a portion of the substrate by incorporating the photochromic material into at least a portion of the polymeric material of the substrate, or by incorporating the photochromic material into at least a portion of the oligomeric or monomeric material from which the substrate is formed. For example, according to one non-limiting embodiment, the photochromic article may be formed from a photochromic composition, such as those discussed above, by the cast-in-place method wherein the photochromic material is incorporated into at least a portion of the polymeric material of the substrate by blending and/or bonding the photochromic material with at least a portion of the polymeric material prior to forming the substrate, or by incorporating the photochromic material into at least a portion of the oligomeric or monomeric material from which the polymeric material of the substrate is formed prior to forming the substrate. According to other non-limiting embodiments, the photochromic material may be incorporated into the polymeric material of the substrate by imbibition. Imbibition and the cast-in-place method are discussed below in more detail.

According to still other non-limiting embodiments, the photochromic material may be connected to at least a portion of the substrate of the photochromic article as part of an at least partial coating that is connected to at least a portion of a substrate. As used herein, the term "coating" means a structure comprising one or more complete or partial layers (which may or may not have a uniform composition and/or cross-sectional thickness) derived from flowable compositions. The flowable compositions from which coatings may be formed include, for example, liquid or powder compositions, which may be applied to the substrate using methods, such as those discussed herein below. According to these non-limiting embodiments, the substrate may be a polymeric substrate or an inorganic substrate (such as, but not limited to, a glass substrate). Examples of monomers and polymers that may be used to form the polymeric substrates according to various non-limiting embodiments disclosed herein include, but are not limited to, those monomers and polymers discussed above that may be useful in forming the photochromic compositions according to various non-limiting embodiments disclosed herein.

According to one non-limiting embodiment disclosed herein, the substrate may be an ophthalmic substrate. As used herein, the term "ophthalmic substrate" refers to lenses, partially formed lenses, and lens blanks. Non-limiting examples of organic-materials from which ophthalmic substrates according to various non-limiting embodiments disclosed herein may be formed include, but are not limited to, art-recognized polymers that are useful in forming transparent or optically clear castings for optical applications (such as those previously discussed).

Other non-limiting examples of organic materials suitable for use in forming the substrates according to various non-limiting embodiments disclosed herein include both synthetic and natural organic materials, including without limitation: opaque or translucent polymeric materials, natural and synthetic textiles, and cellulosic materials. Non-limiting examples of inorganic materials suitable for use in forming substrates that may be used in conjunction with various non-limiting embodiments disclosed herein include inorganic oxide-based glasses, minerals, ceramics, and metals. For example, in one non-limiting embodiment the substrate may comprise glass. In other non-limiting embodiments, the substrate may be a ceramic, metal or mineral substrate that has been polished to form a reflective surface. In other non-limiting embodiments, a reflective coating or layer may be deposited or otherwise applied to a surface of an inorganic or an organic substrate to make it reflective or to enhance its reflectivity.

According to various non-limiting embodiments disclosed herein, the substrate may comprise a protective coating on at least a portion of its surface. As used herein, the term "protective coating" refers to coatings or films that can prevent wear or abrasion, provide a transition in properties from one coating or film to another, protect against the effects of polymerization reaction chemicals and/or protect against deterioration due to environmental conditions, such as, moisture, heat, ultraviolet light, oxygen, etc. For example, commercially available thermoplastic polycarbonate ophthalmic lens substrates are often sold with an abrasion-resistant coating already applied to their surfaces because these surfaces tend to be readily scratched, abraded or scuffed. An example of one such polycarbonate lens substrate is sold under the trademark GENTEX (by Gentex Optics). Non-limiting examples of abrasion-resistant coatings include, abrasion-resistant coatings comprising silanes, abrasion-resistant coatings comprising radiation-cured acrylate-based thin films, abrasion-resistant coatings based on inorganic materials such as silica, titania and/or zirconia, and combinations thereof. For example, according to various non-limiting embodiments, the protective coating may comprise a first coating of a radiation-cured acrylate-based thin film and a second coating comprising a silane. Non-limiting examples of commercial protective coatings products include SILVUE® 124 and HI-GARD® coatings, commercially available from SDC Coatings, Inc. and PPG Industries, Inc., respectively.

According to various non-limiting embodiments disclosed herein, the photochromic material according to various non-limiting embodiments of the present invention discussed above may be incorporated into at least a portion of a coating composition prior to application of the coating composition to the substrate, or alternatively, a coating composition may be applied to the substrate, at least partially set, and thereafter the photochromic material may be imbibed into at least a portion of the coating. As used herein with reference to coatings, coating compositions, or components thereof, the terms "set" and "setting" are intended to include processes, such as, but not limited to, curing, polymerizing, cross-linking, cooling and drying.

Specific non-limiting examples of coating composition into which the photochromic materials according to various non-limiting embodiments disclosed herein may be incorporated include, but are not limited to, those coating compositions known in the art for use in connection with photochromic materials. Non-limiting examples of a coating compositions into which the photochromic materials according to various non-limiting embodiments disclosed herein may be incorporated include the mono-isocyanate containing coating compositions disclosed in U.S. Pat. No. 6,916,537 ("the '537 patent") at col. 3, lines 1 to 12, which comprises (in addition to a photochromic material) a reaction product (non-limiting examples which are set forth in the '537 patent at col. 7, lines 4-37) of a polyol comprising at least one carbonate group (non-limiting examples of which are set forth in the '537 patent at col. 7, line 38 to col. 8, line 49) and an isocyanate comprising at least one reactive isocyanate group and at least one polymerizable double bond (non-limiting examples of which are set forth in the '537 patent at col. 8, line 50 to col. 9, line 44), and which optionally comprises an addition copolymerizable monomer (non-limiting examples of which are set forth in the '537 patent at col. 11, line 47 to col. 20, line 43). The above-referenced disclosure of the '537 patent is hereby specifically incorporated by reference herein.

Other non-limiting examples of coating compositions into which the photochromic materials according to various non-limiting embodiments disclosed herein may be incorporated include the poly(urea-urethane) compositions disclosed in U.S. Pat. No. 6,531,076, at col. 3, line 4 to col. 10, line 49, which disclosure is hereby specifically incorporated by reference herein. Still other non-limiting examples of coating compositions into which the photochromic materials according to various non-limiting embodiments disclosed herein may be incorporated include the polyurethane compositions disclosed in U.S. Pat. No. 6,187,444, at col. 2, line 52 to col. 12, line 15, which disclosure is hereby specifically incorporated by reference herein.

Yet other non-limiting examples of coating compositions into which the photochromic materials according to various non-limiting embodiments disclosed herein may be incorporated include the poly(meth)acrylic coating compositions described in U.S. Pat. No. 6,602,603, at col. 2, line 60 to col. 7, line 50; the aminoplast resin coating compositions described in U.S. Pat. No. 6,506,488, at col. 2, line 43 to col. 12, line 23 and U.S. Pat. No. 6,432,544, at col. 2, line 32 to col. 14, line 5; the polyanhydride coating compositions described in U.S. Pat. No. 6,436,525, at col. 2, line 15 to col. 11, line 60; the epoxy resin coating compositions described in U.S. Pat.

No. 6,268,055, at col. 2, line 63 to col. 17, line 3; and the alkoxyacrylamide coating compositions descried in U.S. Pat. No. 6,060,001, at col. 2, line 6 to col. 5, line 39. The above-referenced disclosures are hereby specifically incorporated by reference herein.

Further, it will be appreciated by those skilled in the art that the photochromic coating compositions according to various non-limiting embodiments disclosed herein may further comprise other additives that aid in the processing and/or performance of the composition or coating derived therefrom. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

According to one non-limiting embodiment, an at least partial coating comprising the photochromic material may be connected to at least a portion of a substrate of a photochromic article, for example, by applying a coating composition comprising the photochromic material to at least a portion of a surface of the substrate and at least partially setting the coating composition. Additionally or alternatively, the at least partial coating comprising the photochromic material may be connected to the substrate, for example, through one or more additional at least partial coatings. For example, while not limiting herein, according to various non-limiting embodiments, an additional coating composition may be applied to a portion of the surface of the substrate, at least partially set, and thereafter a coating composition comprising the photochromic material may be applied over the additional coating and at least partially set. Non-limiting methods of applying coatings compositions to substrates are discussed herein.

Non-limiting examples of additional coatings and films that may be used in conjunction with the photochromic articles disclosed herein include primer or compatiblizing coatings; protective coatings, including transitional coatings, abrasion-resistant coatings and other coatings that protect against the effects of polymerization reaction chemicals and/or protect against deterioration due to environmental conditions, such as, moisture, heat, ultraviolet light, and/or oxygen (e.g., UV-shielding coatings and oxygen barrier coatings); anti-reflective coatings; conventional photochromic coating; polarizing coatings and polarizing stretched-films; and combinations thereof.

Non-limiting examples of primer or compatiblizing coatings that may be used in conjunction with various non-limiting embodiments disclosed herein include coatings comprising coupling agents, at least partial hydrolysates of coupling agents, and mixtures thereof. As used herein, the term "coupling agent" means a material having a group capable of reacting, binding and/or associating with a group on a surface. Coupling agents according to various non-limiting embodiments disclosed herein may include organometallics, such as, silanes, titanates, zirconates, aluminates, zirconium aluminates, hydrolysates thereof, and mixtures thereof. As used herein, the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating" means a coating that aids in creating a gradient in properties between two coatings. For example, although not limiting herein, a transitional coating may aid in creating a gradient in hardness between a relatively hard coating (such as, an abrasion-resistant coating) and a relatively soft coating (such as, a photochromic coating). Non-limiting examples of transitional coatings include radiation-cured, acrylate-based thin films as described in U.S. Patent Application Publication No. 2003/0165686 at paragraphs [0079]-[0173], which disclosure is hereby specifically incorporated by reference herein.

As used herein, the term "abrasion-resistant coating" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion-resistant coatings include abrasion-resistant coatings comprising organosilanes, organosiloxanes, abrasion-resistant coatings based on inorganic materials such as silica, titania and/or zirconia, and organic abrasion-resistant coatings of the type that are UV-light curable.

Non-limiting examples of antireflective coatings include a monolayer coating or multilayer coatings of metal oxides, metal fluorides, or other such materials, which may be deposited onto the articles disclosed herein (or onto self supporting films that are applied to the articles), for example, through vacuum deposition, sputtering, etc.

Non-limiting examples of polarizing coatings and polarizing stretched-films include, but are not limited to, polarizing coatings (such as those described in U.S. Patent Application Publication No. 2005/0151926, at paragraphs [0029]-[0116], which disclosure is hereby specifically incorporated by reference herein), and polarizing stretched-films comprising dichroic compounds that are known in the art.

As discussed above, according to various non-limiting embodiments an additional at least partial coating or film may be formed on the substrate prior to forming the coating comprising the photochromic material according to various non-limiting embodiments disclosed herein on the substrate. For example, according to certain non-limiting embodiments a primer or compatiblizing coating may be formed on the substrate prior to applying the coating composition comprising the photochromic material. Additionally or alternatively, one or more additional at least partial coating(s) may be formed on the substrate after forming the coating comprising the photochromic material, according to various non-limiting embodiments disclosed herein, on the substrate, for example, as an overcoating on the photochromic coating. For example, according to certain non-limiting embodiments, a transitional coating may be formed over the coating comprising the photochromic material, and an abrasion-resistant coating may then be formed over the transitional coating.

For example, according to certain non-limiting embodiments there is provided a photochromic article comprising a substrate (such as, but not limited to a plano-concave or a plano-convex ophthalmic lens substrate), which comprises an abrasion-resistant coating on at least a portion of a surface thereof; a primer or compatiblizing coating on at least a portion of the abrasion-resistant coating; a photochromic coating comprising a photochromic material, according to various non-limiting embodiments disclosed herein, on at least a portion of the primer or compatiblizing coating; a transitional coating on at least a portion of the photochromic coating; and an abrasion-resistant coating on at least a portion of the transitional coating. Further, according to other non-limiting embodiments, the photochromic article may also comprise, for example, an antireflective coating that is connected to a surface of the substrate and/or a polarizing coating or film that is connected to a surface of the substrate.

One non-limiting embodiment of the present invention provides a method of making a photochromic composition, the method comprising incorporating a photochromic material, according to any of the various non-limiting embodiments of the present invention, into at least a portion of an organic material. Non-limiting methods of incorporating photochromic materials into an organic material include, for example, mixing the photochromic material into a solution or melt of a polymeric or oligomeric material, and subsequently at least partially setting the polymeric or oligomeric material (with or without bonding the photochromic material to the organic material); mixing the photochromic material with a monomeric material and subsequently at least partially polymerizing the monomer (with or without co-polymerizing the photochromic material with the monomer or otherwise bonding the photochromic material to the resultant polymer or intermediate in the polymerization reaction as previously discussed); and imbibing the photochromic material into a polymeric material (with or without bonding the photochromic material to the polymeric material).

Another non-limiting embodiment provides a method of making a photochromic article comprising connecting a photochromic material, according to any of the various non-limiting embodiments discussed above, to at least a portion a substrate. For example, if the substrate is formed from a polymeric material, the photochromic material may be connected to at least a portion of the substrate by the cast-in-place method and/or by imbibition. For example, in the cast-in-place method, the photochromic material may be mixed with a polymeric solution or melt, or other oligomeric and/or monomeric solution or mixture, which may be subsequently cast into a mold having a desired shape and at least partially set to form the substrate. Optionally, according to this non-limiting embodiment, the photochromic material may be bonded to a portion of the polymeric material of the substrate, for example, by co-polymerization with a monomeric precursor thereof or an intermediate in the polymerization reaction. In the imbibition method, the photochromic material may be diffused into the polymeric material of the substrate after it is formed, for example, by immersing a substrate in a solution containing the photochromic material, with or without heating. Thereafter, although not required, the photochromic material may be bonded with the polymeric material.

Other non-limiting embodiments disclosed herein provide methods of making an photochromic article comprising connecting a photochromic material, according to any of the various non-limiting embodiments discussed above, to at least a portion of a substrate by at least one of in-mold casting, coating and lamination.

For example, according to one non-limiting embodiment wherein the substrate comprises a polymeric material, the photochromic material may be connected to at least a portion of a substrate by in-mold casting. According to this non-limiting embodiment, a coating composition comprising the photochromic material, which may be a liquid coating composition or a powder coating composition, may be applied to the surface of a mold and at least partially set. Thereafter, a polymer solution or melt, or oligomeric or monomeric solution or mixture may be cast over the coating and at least partially set. After setting, the coated substrate may be removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

According to still other non-limiting embodiments, wherein the substrate comprises a polymeric material or an inorganic material, such as, for example, glass, the photochromic material may be connected to at least a portion of a substrate by a coating process. Non-limiting examples of suitable coating processes include spin coating, spray coating (e.g., using a liquid or a powder coating compositions), curtain coating, roll coating, spin and spray coating, dip coating, over-molding, and combinations thereof. For example, according to one non-limiting embodiment, the photochromic material may be connected to the substrate by over-molding. According to this non-limiting embodiment, a coating composition comprising the photochromic material (examples of which coatings are discussed above) may be applied to a mold and then a substrate may be placed into the mold such that the substrate contacts the coating causing it to spread over at least a portion of the surface of the substrate. Thereafter, the coating composition may be at least partially set and the coated substrate may be removed from the mold. Alternatively, the over-molding process may comprise placing the substrate into a mold such that an open region is defined between the substrate and the mold, and thereafter injecting a coating composition comprising the photochromic material into the open region. Thereafter, the coating composition may be at least partially set and the coated substrate may be removed from the mold. According to another non-limiting embodiment, the photochromic material may be connected to a substrate by spin-coating a coating composition comprising the photochromic material onto the substrate, for example, by rotating the substrate and applying the coating composition to the substrate while it is rotating and/or by applying the coating composition to the substrate and subsequently rotating the substrate.

Additionally or alternatively, a coating composition (with or without a photochromic material) may be applied to a substrate (for example, by any of the foregoing coating processes), the coating composition may be at least partially set, and thereafter, a photochromic material according to any of the various non-limiting embodiments disclosed herein may be imbibed (as previously discussed) into the coating.

As discussed above, according to various non-limiting embodiments disclosed herein, after forming the photochromic coating, at least a portion of the photochromic coating may be at least partially set. For example, according to various non-limiting embodiments disclosed herein, at least partially setting at least a portion of the photochromic coating may comprise exposing the photochromic coating to at least one of electromagnetic radiation and thermal radiation to at least partially dry, polymerize and/or cross-link one or more components of the coating composition.

According to yet another non-limiting embodiment, wherein the substrate comprises a polymeric material or an inorganic material, such as, for example, glass, the photochromic material may be connected to at least a portion of a substrate by lamination. For example, according to this non-limiting embodiment, a self-supporting film or sheet comprising the photochromic material may be adhered or otherwise connect to a portion of the substrate, with or without an adhesive and/or the application of heat and pressure. Optionally, thereafter a protective coating may be applied over the film; or a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include, for example and without limitation, combining a photochromic material with a polymeric or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, according to various non-limiting embodiments, prior to connecting the photochromic material to at least a portion of the substrate by any of coating and lamination, a primer or compatiblizing coating (such as those discussed above) may be formed on at least a portion of the surface of the substrate to enhance one or more of the wetting, adhesion, and/or chemical compatibility of the photochromic coating with the substrate. Non-limiting examples of suitable primer or compatiblizing coatings and methods of making the same are disclosed above. Still further, as previously discussed according to various non-limiting embodiments disclosed herein, the substrate may comprise an abrasion-resistant coating on at least a portion of its surface.

According to various non-limiting embodiments disclosed herein, prior to applying any coating or film to the substrate, for example, prior to connecting the photochromic material to at least a portion of the surface of the substrate by coating and/or lamination or prior to applying a primer or compatiblizing coating to the substrate, the surface may be cleaned and/or treated to provide a clean surface and/or a surface that may enhance adhesion of the photochromic coating to the substrate. Effective cleaning and treatments may include, but are not limited to, ultrasonic washing with an aqueous soap/detergent solution; cleaning with an aqueous mixture of organic solvent, e.g., a 50:50 mixture of isopropanol:water or ethanol:water; UV treatment; activated gas treatment, e.g., treatment with low temperature plasma or corona discharge; and chemical treatment that results in hydroxylation of the substrate surface, e.g., etching of the surface with an aqueous solution of alkali metal hydroxide, e.g., sodium or potassium hydroxide, which solution can also contain a fluorosurfactant. Generally, the alkali metal hydroxide solution is a dilute aqueous solution, e.g., from 5 to 40 weight percent, more typically from 10 to 15 weight percent, such as 12 weight percent, alkali metal hydroxide. See, for example, U.S. Pat. No. 3,971,872, column 3, lines 13 to 25; U.S. Pat. No. 4,904,525, column 6, lines 10 to 48; and U.S. Pat. No. 5,104,692, column 13, lines 10 to 59, which describe surface treatments of polymeric organic materials. The foregoing disclosures are specifically incorporated herein by reference.

In one non-limiting embodiment, surface treatment of the substrate may be a low temperature plasma treatment. Although not limiting herein, this method allows treatment of the surface to enhance adhesion of a coating formed thereon, and may be a clean and efficient way to alter the physical surface, e.g., by roughening and/or chemically altering the surface without affecting the rest of the article. Inert gases, such as argon, and reactive gases, such as oxygen, may be used as the plasma gas. Inert gases may roughen the surface, while reactive gases such as oxygen may both roughen and chemically alter the surface exposed to the plasma, e.g., by producing hydroxyl or carboxyl units on the surface. According to one non-limiting embodiment, oxygen may be used as the plasma gas. Although not limiting herein, it is considered that oxygen may provides a slight, but effective, physical roughening of the surface along with a slight, but effective, chemical modification of the surface. As will be appreciated by those skilled in the art, the extent of the surface roughening and/or chemical modification will be a function of the plasma gas and the operating conditions of the plasma unit (including the length of time of the treatment).

The surface of the substrate subjected to plasma treatment may be at room temperature or may be preheated slightly prior to or during plasma treatment. Although not limiting herein, according to various embodiments, the temperature of the surface to be subjected to a plasma treatment may be maintained at a temperature below a temperature at which the surface may be adversely affected by the plasma (other than the intended increase in surface area by roughening and slight chemical modification). One skilled in the art can readily select operating conditions of the plasma unit, vis-à-vis, the plastic substrate treated, to achieve an improvement in the adhesion of a superimposed film/coating on the plasma treated surface.

Various non-limiting embodiments disclosed herein further contemplate the use of various combinations of the forgoing methods to form photochromic articles according to various non-limiting embodiments disclosed herein. For example, and without limitation herein, according to one non-limiting embodiment, a photochromic material may be connected to a substrate by incorporation into an organic material from which the substrate is formed (for example, using the cast-in-place method and/or imbibition), and thereafter a photochromic materials (which may be the same or different from the aforementioned photochromic material) may be connected to a portion of the substrate using the in-mold casting, coating, and/or lamination methods discussed above.

According to various non-limiting embodiments, the photochromic materials described herein may be used in amounts (or ratios) such that the organic material or substrate into which the photochromic materials are incorporated or otherwise connected exhibits desired optical properties. For example, the amount and types of photochromic materials may be selected such that the organic material or substrate may be substantially clear or colorless when the photochromic material is in the ground-state form and may exhibit a desired resultant color when the photochromic material is in the activated-state form. The precise amount of the photochromic material to be utilized in the various photochromic compositions, photochromic coatings and coating compositions, and photochromic articles described herein is not critical provided that a sufficient amount is used to produce the desired effect. It should be appreciated that the particular amount of the photochromic material used may depend on a variety of factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that may be incorporated into an organic material may range from 0.01 to 40 weight percent based on the weight of the organic material.

Various non-limiting embodiments of the present invention will be better understood when read in conjunction with the following non-limiting examples. The procedures set forth in the Examples below are not intended to be limiting herein, as those skilled in the art will appreciate that modifications to the procedures set forth in the Examples, as well as other procedures not described in the Examples, may be useful in preparing photochromic materials according to the present invention.

EXAMPLES

In Part 1 of the Examples, the synthesis procedures used to make photochromic materials according to various non-limiting embodiments disclosed herein are set forth in Examples 1-6, and the procedures used to make a comparative photochromic material are described in Comparative Examples (CE) 1 and 2. In Part 2, the test procedures and results are described.

Part 1: Synthesis Procedures

Example 1

Step 1

Ferrocene (20 g) and benzoyl chloride (15 mL) in 100 mL of methylene chloride were added to a reaction flask fitted with a solid addition funnel under a nitrogen atmosphere. Solid anhydrous aluminum chloride (19.0 g) was added to the reaction mixture with occasionally cooling of the reaction mixture in an ice/water bath. The reaction mixture was stirred at room temperature for 3 hours. The resulting mixture was poured into 200 mL of a 1:1 mixture of ice and 1N HCl and stirred vigorously for 15 minutes. The mixture was extracted three times with 100 mL methylene chloride. The organic extracts were combined and washed with 200 mL of saturated aqueous sodium chloride solution and dried over sodium sulfate. The solution was then filtered and the filtrate concentrated to give 40.0 g of a red oily residue. The product was used in the subsequent reaction without further purification.

Step 2

The crude product from Step 1 (40 g) was dissolved in anhydrous dimethylformamide (100 mL) in a reaction flask with overhead stirring. Sodium acetylide paste in toluene (90 g, ~9 wt %) was added to the reaction flask under vigorous stirring. After the reaction was complete, the mixture was added to ice water (250 mL), and the solution was extracted with ethyl ether (twice with 300 mL). The organic extracts were combined and washed with saturated aqueous sodium chloride solution and dried over sodium sulfate. The solution was then filtered and the filtrate concentrated to give a dark residue (50 g). The product was used in the subsequent reaction without further purification.

Step 3

7,7-dimethyl-7H-benzo[C]fluoren-5-ol (2 g, prepared by a similar procedure to the product of Example 5, Step 5 of U.S. Pat. No. 6,296,785, which is hereby specifically incorporated by reference herein), the crude product from Step 2 (5 g), dodecylbenzene sulfonic acid (5 drops) and chloroform (30 mL) were combined in a reaction flask. The mixture was heated at reflux for 3 hours and then concentrated. The residue was purified by silica gel chromatography (ethyl acetate/hexanes (v/v): 1/8). The major fraction was collected from the column and concentrated. The 1.5 g of product was precipitated out from tert-butyl methyl ether/hexanes (v/v:1/1) and filtered off as off-yellow solid. Mass spectrometry analysis supported a molecular weight consistent with 3-phenyl-3-ferrocenyl-13,13-dimethyl-3H,13H-indeno[2',3':3,4]naphtho[1,2-b]pyran.

Example 2

The process of Example 1 was followed except that 4-fluorobenzoyl chloride was used instead of benzoyl chloride in Step 1. Mass spectrometry analysis supported a molecular weight consistent with 3-(4-fluorophenyl)-3-ferrocenyl-13,13-dimethyl-3H,13H-indeno[2',3':3,4]naphtho[1,2-b]pyran.

Example 3

The process of Example 2 (above) was followed except that 2,3-dimethoxy-7,7-dimethyl-7H-benzo[C]fluoren-5-ol (the product of Example 9, Step 2 of U.S. Pat. No. 6,296,785, which is hereby specifically incorporated by reference herein) was used instead of 7,7-dimethyl-7H-benzo[C]fluoren-5-ol. Mass spectrometry analysis supported a molecular weight consistent with 3-(4-fluorophenyl)-3-ferrocenyl-6,7-dimethoxy-13,13-dimethyl-3H,13H-indeno[2',3':3,4]naphtho[1,2-b]pyran.

Example 4

The process of Example 2 (above) was followed except that 2,3-dimethoxy-7-hydroxy-7-ethyl-7H-benzo[C]fluoren-5-ol (the product of Example 1, Step 3 of U.S. Pat. No. 6,296,785B1 which is hereby specifically incorporated by reference herein) was used instead of 7,7-dimethyl-7H-benzo[C]fluoren-5-ol. Mass spectrometry analysis supported a molecular weight consistent with 3-(4-fluorophenyl)-3-ferrocenyl-6,7-dimethoxy-13-ethyl-13-hydroxy-3H,13H-indeno[2',3':3,4]naphtho[1,2-b]pyran.

Example 5

Step 1

2,3-Dimethoxy-7-hydroxy-7-ethyl-7H-benzo[C]fluoren-5-ol (30 g, the product of Example 1, Step 3 of U.S. Pat. No. 6,296,785B1), morpholino (23 g) and tetrahydrofuran (500 mL) were combined in a dry reaction flask under nitrogen atmosphere and butyl lithium (200 mL, 2.5 M in hexane) was cannulated into the reaction flask with stirring. The mixture was stirred for 30 minutes at room temperature and then carefully poured into ice water. The mixture was extracted with ethyl acetate (3 times with 100 mL each). The extracts were combined and washed with saturated aqueous sodium chloride solution. The solution was dried over $Na_2SO_4$ and filtered. The filtrate was concentrated and the residue was purified by silica gel chromatography (ethyl acetate/hexanes (v/v): 1/1). The major fraction was collected from the column and concentrated, yielding 25 g of a yellow foam. Mass spectrometry analysis supported a molecular weight consistent with 2-morpholino-3-methoxy-7-hydroxy-7-ethyl-7H-benzo[C]fluoren-5-ol.

Step 2

The process of Example 4 (above) was followed except that 2-morpholino-3-methoxy-7-hydroxy-7-ethyl-7H-benzo[C]fluoren-5-ol (from step 1) was used instead of 2,3-methoxy-7-hydroxy-7-ethyl-7H-benzo[C]fluoren-5-ol. Mass spectrometry analysis supported a molecular weight consistent with 3-(4-fluorophenyl)-3-ferrocenyl-6-morpholino-7-methoxy-13-ethyl-13-hydroxy-3H,13H-indeno[2',3':3,4]naphtho[1,2-b]pyran.

Example 6

Step 1

1,2-Dimethoxybenzene (31.4 g) and a solution of 4-bromobenzoyl chloride (50.0 g) in 500 mL of methylene chloride were added to a reaction flask fitted with a solid addition funnel under a nitrogen atmosphere. Solid anhydrous aluminum chloride (60.0 g) was added to the reaction mixture with occasional cooling of the reaction mixture in an ice/water bath. The reaction mixture was stirred at room temperature for 3 hours. The resulting mixture was poured into 300 mL of a 1:1 mixture of ice and 1N HCl and stirred vigorously for 15 minutes. The mixture was extracted twice with 100 mL of methylene chloride. The organic extracts were combined and washed with 50 mL of 10 wt % NaOH followed by 50 mL of water. The methylene chloride solvent was removed by rotary evaporation to give 75.0 g of a yellow solid. Nuclear magnetic resonance ("NMR") spectroscopy showed the product to have a structure consistent with 3,4-dimethoxy-4'-bromobenzophenone.

Step 2

Potassium t-butoxide (33 g) and 70.0 g of 3,4-dimethoxy-4'-bromobenzophenone from Step 1 were added to a reaction flask containing 500 mL of toluene under a nitrogen atmosphere. The mixture was heated to reflux and dimethyl succinate (63.7 g) was added dropwise over 1 hour. The mixture was heated to reflux for 5 hours and then cooled to room temperature. The resulting mixture was poured into 300 mL of water and vigorously stirred for 20 minutes. The aqueous and organic phases were separated and the organic phase was extracted with three 100 mL portions of water. The combined aqueous layers were washed with three 150 mL portions of chloroform. The aqueous layer was acidified to pH 2 with 6N HCl and a precipitate was formed. The aqueous layer was extracted with three 100 mL portions of chloroform. The organic extracts were combined and concentrated by rotary evaporation. NMR spectroscopy of the resulting oil showed the product to have structures consistent with a mixture of (E and Z) 4-(3,4-dimethoxypphenyl)-4-(4-bromophenyl)-3-methoxycarbonyl-3-butenoic acids.

Step 3

The crude half esters from Step 2 (100 g) and 60 mL of acetic anhydride were added to a reaction flask under a nitrogen atmosphere. The reaction was heated to 140° C. for 6 hours, cooled to room temperature, and the acetic anhydride removed by rotary evaporation. The residue was dissolved in 300 mL of methylene chloride and 200 mL of water. Solid Na$_2$CO$_3$ was added to the biphasic mixture until bubbling ceased. The layers were separated and the aqueous layer was extracted with 500 mL portions of methylene chloride. The organic extracts were combined and the solvent was removed by rotary evaporation to yield a thick red oil. The oil was dissolved in warm methanol and chilled at 0° C. for 2 hours. The resulting crystals were collected by vacuum filtration, washed with cold methanol to produce the mixtures of 1-(4-bromophenyl)-2-methoxycarbonyl-4-acetoxy-6,7-dimethoxynaphthalene and 1-(3,4-dimethoxyphenyl)-2-methoxycarbonyl-4-acetoxy-6-bromonaphthalene. The produce mixture was used without further purification in the subsequent reaction.

Step 4

The mixture (50.0 g) from Step 3 was weighed into a reaction flask under a nitrogen atmosphere and 300 mL of anhydrous THF was added. Methyl magnesium chloride (200 mL of 3.0M in THF) was added to the reaction mixture over 1 hour. The reaction mixture was stirred overnight and then poured into 300 mL of a 1:1 mixture of ice and 1N HCl. The mixture was extracted with chloroform (three times with 300 mL). The organic extracts were combined, washed with saturated aqueous NaCl solution (400 mL) and dried over anhydrous Na$_2$SO$_4$. Removal of the solvent by rotary evaporation yielded 40.0 g of 1-(4-bromophenyl)-2-(dimethylhydroxymethyl)-4-hydroxy-6,7-dimethoxynaphthalene and 1-(3,4-dimethoxyphenyl)-2-(dimethylhydroxymethyl)-4-hydroxy-6-bromonaphthalene.

Step 5

The products from Step 4 (30.0 g) were placed in a reaction flask equipped with a Dean-Stark trap and 150 mL of toluene was added. The reaction mixture was stirred under a nitrogen atmosphere and dodecylbenzene sulfonic acid (about 0.5 mL) was added. The reaction mixture was heated at reflux for 2 hours and then cooled to room temperature. Upon cooling the mixture to room temperature for 24 hours, the white solid was precipitated. NMR spectroscopy showed the product to have a structure consistent with 2,3-dimethoxy-7,7-dimethyl-9-bromo-7H-benzo[C]fluoren-5-ol. This material was not purified further but was used directly in the next step.

Step 6

2,3-Dimethoxy-7,7-dimethyl-9-bromo-benzo[C]fluoren-5-ol from Step 5 (30 g), tetrakis(triphenylphosphine)palladium(0) (2 g), phenylboronic acid (12 g), sodium carbonate (18 g), ethylene glycol dimethyl ether (300 mL), and water (60 mL) were combined in a reaction flask under a nitrogen atmosphere and stirred for 1 hour at room temperature. The mixture was then heated at reflux for 24 hours. After this time, the mixture was cooled to room temperature and neutralized with 10% hydrochloric acid. The mixture was extracted with methylene chloride (three times with 300 mL). The organic extracts were combined and the solvent was removed by rotary evaporation to give 30 g of off-white solid. NMR spectroscopy showed the product to have a structure consistent with 2,3-dimethoxy-7,7-dimethyl-9-phenyl-7H-benzo [C]fluoren-5-ol.

Step 7

The process for Step 3 of Example 3 (above) was followed except that 2,3-dimethoxy-9-phenyl-7,7-dimethyl-7H-benzo [C]fluoren-5-ol (from Step 6) was used instead of 2,3-dimethoxy-7,7-dimethyl-7H-benzo[C]fluoren-5-ol. Mass spectrometry analysis supported a molecular weight consistent with 3-(4-fluorophenyl)-3-ferrocenyl-6,7-dimethoxy-11-phenyl-13,13-dimethyl-3H,13H-indeno[2',3':3,4]naphtho[1,2-b]pyran.

COMPARATIVE EXAMPLES

Comparative Example 1 (CE1)

Step 1

4-Fluorobenzophenone (30 g), morpholine (13 g), potassium carbonate (20 g) and dimethyl sulfoxide (100 mL) were added in a reaction flask equipped with a condenser. The mixture was heated to 100° C. for overnight, and then cooled to room temperature. The mixture was poured into cold water (400 mL) and the slurry was extracted with chloroform (2×200 mL). The organic layers were separated, combined, dried over sodium sulfate and filtered. The filtrate was concentrated to give an orange colored oil (45 g). The product was used in next step without further purification.

Step 2

The process for Step 2 of Example 1 was followed except that 4-morpholinobenzophenone (from Step 1) was used instead of ferrocenyl 4-fluorophenyl ketone to provide 1-(4-morpholinophenyl)-1-phenyl-2-propyn-1-ol.

Step 3

The process for Step 3 of Example 1 was followed except that 1-(4-morpholinophenyl)-1-phenyl-2-propyn-1-ol (from Step 2) was used instead of 1-ferrocenyl-1-phenyl-2-propyn-1-ol to react with 7,7-dimethyl-7H-benzo[C]fluoren-5-ol to provide 3-phenyl-3-(4-morpholinophenyl)-13,13-dimethyl-3H,13H-indeno[2',3':3,4]naphtho[1,2-b]pyran. Mass spectrometry analysis supported a molecular weight consistent with 3-phenyl-3-(4-morpholinophenyl)-13,13-dimethyl-3H,13H-indeno[2',3':3,4]naphtho[1,2-b]pyran.

Comparative Example 2 (CE2)

Step 1

The process for Step 2 of Example 1 was followed except that 4-fluorobenzophenone was used instead of ferrocenyl 4-fluorophenyl ketone to provide 1-(4-fluorophenyl)-1-phenyl-2-propyn-1-ol.

Step 2

The process from Step 3 of Example 1 was followed except that 1-(4-fluorophenyl)-1-phenyl-2-propyn-1-ol (from Step 1) was used instead of 1-ferrocenyl-1-(4-fluorophenyl)-2-propyn-1-ol. The 1-(4-fluorophenyl)-1-phenyl-2-propyn-1-ol was reacted with 7,7-dimethyl-7H-benzo[C]fluoren-5-ol (from Step 3 of Example 1) to provide 3-phenyl-3-(4-fluorophenyl)-13,13-dimethyl-3H,13H-indeno[2',3':3,4]naphtho[1,2-b]pyran. Mass spectrometry analysis supported a molecular weight consistent with 3-phenyl-3-(4-fluorophenyl)-13,13-dimethyl-3H,13H-indeno[2',3':3,4]naphtho[1,2-b]pyran.

Part 2: Test Procedures and Results

The photochromic performance of the photochromic materials of Examples 1-6 and Comparative Examples 1-2 were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a diamond blade saw into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 23° C. (73° F.). The bench was fitted with a 300-watt xenon arc lamp, a remote controlled shutter, a Melles Griot KG2 filter that modifies the UV and IR wavelengths and acts as a heat-sink, neutral density filter(s) and a sample holder, situated within a water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max\text{-}vis}$ is the wavelength in the visible spectrum at which the maximum absorption of the activated-state form of the photochromic compound in a test square occurs. The $\lambda_{max\text{-}vis}$ wavelength was determined by testing the photochromic test squares in a Varian Cary 300 UV-Visible spectrophotometer; it may also be calculated from the spectrum obtained by the S2000 spectrometer on the optical bench.

The saturated optical density ("Sat'd OD") for each test square was determined by opening the shutter from the xenon lamp and measuring the transmittance after exposing the test chip to UV radiation for 30 minutes. The $\lambda_{max\text{-}vis}$ at the Sat'd OD was calculated from the activated data measured by the S2000 spectrometer on the optical bench. The First Fade Half Life ("$T_{1/2}$") is the time interval in seconds for the absorbance of the activated-state form of the photochromic material in the test squares to reach one half the Sat'd OD absorbance value at room temperature (73° F.), after removal of the source of activating light.

Results for the photochromic materials tested are listed below in Table 1.

TABLE 1

Photochromic Test Data

| Example No. | $T_{1/2}$ (sec) | Sat'd OD (at $\lambda_{max\text{-}vis}$) | $\lambda_{max\text{-}vis}$ (nm) |
|---|---|---|---|
| 1 | 206 | 0.35 | 648 |
| 2 | 142 | 0.15 | 648 |
| 3 | 236 | 0.38 | 647 |
| 4 | 73 | 0.16 | 654 |
| 5 | 83 | 0.19 | 654 |
| 6 | 234 | 0.36 | 653 |
| CE1 | 241 | 1.45 | 583 |
| CE2 | 542 | 1.53 | 541 |

The photochromic materials of Examples 1 and 2 were observed to exhibit a greenish blue color, Examples 3-6 were observed to exhibit a greenish color, whereas the Comparative Example 1 was observed to exhibit a deep blue color and the Comparative Example 2 was observed to exhibit a purple-pink color.

Further, in comparing the photochromic performance results in Table 1 for Example 1 (i.e., 3-phenyl-3-ferrocenyl-13,13-dimethyl-3H,13H-indeno[2',3':3,4]naphtho[1,2-b]pyran) and the Comparative Example 1 (i.e., 3-phenyl-3-(4-morpholinophenyl)-13,13-dimethyl-3H,13H-indeno[2',3':3,4]naphtho[1,2-b]pyran), it can be seen that the Example 1 material had a faster fade rate (i.e., smaller $T_{1/2}$ value) than Comparative Example 1. Further, the fade rate of Example 2 (i.e., 3-(4-fluorophenyl)-3-ferrocenyl-13,13-dimethyl-3H,13H-indeno[2',3':3,4]naphtho[1,2-b]pyran) is faster (i.e., smaller $T_{1/2}$ value) than the fade rate of Comparative Example 2 (i.e., 3-phenyl-3-(4-fluorophenyl)-13,13-dimethyl-3H,13H-indeno[2',3':3,4]naphtho[1,2-b]pyran). These compounds (i.e., Example 1 and CE1 and Example 2 and CE2) have directly related structural features, differing only in the replacement of a phenyl at the 3-position of the indeno-fused naphthopyran with the ferrocenyl group. Thus, the increase in fade rate and characteristic greenish color of the absorption spectrum may be due to the presence of the metallocenyl group at the 3-position of the indeno-fused naphthopyran. The fade rates values obtained for Examples 3-6 are not believed to be directly comparable to the fade rates values obtained for the Comparative Examples owing to structural differences other than the ferrocenyl group.

As previously discussed, while the present invention is described herein in connection with certain embodiments and examples, the present invention is not limited to the particular embodiments and examples disclosed, but is intended to cover modifications that are within the spirit and scope of the invention, as defined by the appended claims. Further, it is to be understood that the present description illustrates aspects of the invention relevant to a clear understanding of the invention. Accordingly, certain aspects of the invention that would be apparent to those of ordinary skill in the art and that, therefore, would not facilitate a better understanding of the invention have not been presented in order to simplify the present description.

What is claimed is:

1. A photochromic material comprising:
   (a) an indeno-fused naphthopyran, and
   (b) a metallocenyl group bonded to at least one available position on the indeno-fused naphthopyran, wherein the indeno-fused naphthopyran is an indeno[2',3':3,4]naphtho[1,2-b]pyran, and the metallocenyl group is bonded to at least one of the 6-position, the 7-position, the 10-position, the 11-position or the 13-position of the indeno[2',3':3,4]naphtho[1,2-b]pyran.

2. The photochromic material of claim 1 wherein the metallocenyl group is at least one of a ferrocenyl group, a titanocenyl group, a ruthenocenyl group, and a chromocenyl group.

3. The photochromic material of claim 1 wherein the metallocenyl group is a ferrocenyl group.

4. The photochromic material of claim 1 wherein the metallocenyl group is represented by at least one of structure (ii) or structure (iii):

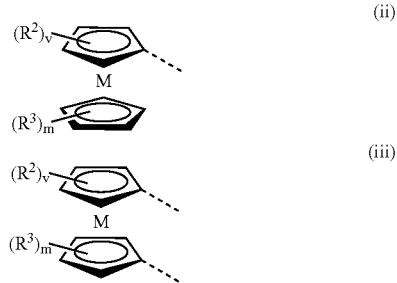

wherein

M is Ti, V, Cr, Mn, Fe, Ru, Os, Co or Ni;

v and m are each integers from 0 to 3;

each $R^2$ is independently halogen, $C_1$-$C_3$ alkyl, phenyl($C_1$-$C_3$) alkyl, $C_1$-$C_3$ alkoxy, phenyl($C_1$-$C_3$) alkoxy, amino, vinyl or —C(O)$R^4$, wherein $R^4$ is hydrogen, hydroxy, $C_1$-$C_3$ alkyl or phenyl; or two adjacent $R^2$ groups, together form benzo; and $R^3$ is halogen, $C_1$-$C_3$ alkyl, phenyl($C_1$-$C_3$) alkyl, $C_1$-$C_3$ alkoxy, phenyl($C_1$-$C_3$) alkoxy, amino, vinyl, a photochromic group or —C(O)$R^4$, wherein $R^4$ is hydrogen, hydroxy, $C_1$-$C_3$ alkyl or phenyl.

5. The photochromic material of claim 1 wherein photochromic material displays a green or greenish color when exposed to actinic radiation.

6. A photochromic composition comprising the photochromic material of claim 1 incorporated into at least a portion of an organic material, said organic material being a polymeric material, an oligomeric material, a monomeric material or a mixture or combination thereof.

7. A photochromic article comprising a substrate and a photochromic material according to claim 1 connected to at least a portion of the substrate.

8. The photochromic article of claim 7 wherein the photochromic article is an optical element, said optical element being at least one of an ophthalmic element, a display element, a window, a mirror, and a liquid crystal cell element.

9. The photochromic article of claim 8 wherein the optical element is an ophthalmic element, said ophthalmic element being at least one of a corrective lens, a non-corrective lens, a magnifying lens, a protective lens, a visor, goggles and a lens for an optical instrument.

10. The photochromic article of claim 7 wherein the substrate comprises a polymeric material and the photochromic material is incorporated into at least a portion of the polymeric material by at least one of blending, bonding, and imbibing.

11. The photochromic article of claim 7 wherein the photochromic article comprises an at least partial coating connected to at least a portion of the substrate, said at least partial coating comprising the photochromic material.

12. The photochromic article of claim 11 wherein the photochromic article further comprises a protective coating on at least a portion of the at least partial coating comprising the photochromic material.

13. A photochromic material represented by:

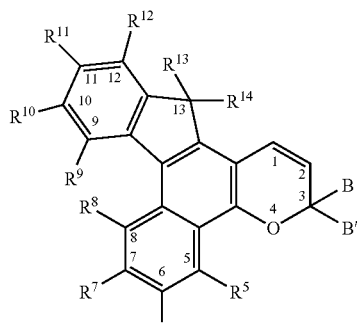

wherein:

B and B' are each independently:
  (a) an aryl group that is mono-substituted with a reactive substituent or a compatiblizing substituent;
  (b) 9-julolidinyl, an unsubstituted, mono-, di- or tri-substituted aryl group chosen from phenyl and naphthyl, an unsubstituted, mono-or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, wherein the aryl and heteroaromatic substituents are each independently:
    hydroxy, aryl, mono- or di-($C_1$-$C_{12}$)alkoxyaryl, mono- or di-($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$) alkyl, aryloxy($C_1$-$C_{12}$)alkoxy, mono- or di-($C_1$-$C_{12}$)alkylaryl($C_1$-$C_{12}$)alkyl, mono- or di-($C_1$-$C_{12}$) alkoxyaryl($C_1$-$C_{12}$)alkyl, mono- or di-($C_1$-$C_{12}$) alkylaryl($C_1$-$C_{12}$)alkoxy, mono- or di-($C_1$-$C_{12}$) alkoxyaryl($C_1$-$C_{12}$)alkoxy, amino, mono- or di-($C_1$-$C_{12}$)alkylamino, diarylamino, piperazino, N-($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidino, $C_1$-$C_{12}$ alkyl, $C_1$-$C_{12}$ haloalkyl, $C_1$-$C_{12}$ alkoxy, mono($C_1$-$C_{12}$)alkoxy ($C_1$-$C_{12}$)alkyl, acryloxy, methacryloxy, halogen or —C(=O)$R^{15}$, wherein $R^{15}$ is —$OR^{16}$, —N($R^{17}$) $R^{18}$, piperidino or morpholino, wherein $R^{16}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R^{17}$ and $R^{18}$ are each independently $C_1$-$C_6$ alkyl, $C_5$-$C_7$ cycloalkyl or a substituted or unsubstituted phenyl, wherein said phenyl substituents are each independently $C_1$-$C_6$ alkyl or $C_1$-$C_6$ alkoxy;

(c) an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, said substituents being $C_1$-$C_{12}$ alkyl, $C_1$-$C_{12}$ alkoxy, phenyl or halogen;

(d) a 4-substituted phenyl, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$— or —[O—(CH$_2$)$_e$]$_f$—, wherein e is an integer ranging from 2 to 6 and f is an integer ranging from 1 to 50, and wherein the substituent is connected to an aryl group on another photochromic material;

(e) a group represented by:

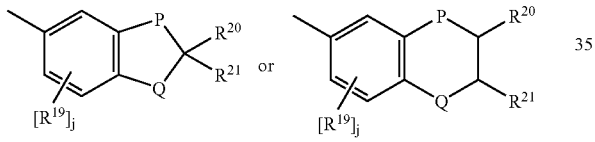

wherein P is —CH$_2$— or —O—; Q is —O— or substituted nitrogen, provided that when Q is substituted nitrogen, P is —CH$_2$—, the substituted nitrogen substituents being hydrogen, $C_1$-$C_{12}$ alkyl or $C_1$-$C_{12}$ acyl; each $R^{19}$ is independently $C_1$-$C_{12}$ alkyl, $C_1$-$C_{12}$ arkoxy, hydroxy or halogen; $R^{20}$ and $R^{21}$ are each independently hydrogen or $C_1$-$C_{12}$ alkyl; and j is an integer ranging from 0 to 2; or (f) a group represented by:

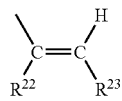

wherein $R^{22}$ is hydrogen or $C_1$-$C_{12}$ alkyl, and $R^{23}$ is an unsubstituted, mono- or di-substituted naphthyl, phenyl, furanyl or thienyl, wherein said naphthyl, phenyl, furanyl and thienyl substituents are each independently $C_1$-$C_{12}$ alkyl, $C_1$-$C_{12}$ alkoxy or halogen; or B and B' taken together form a fluoren-9-ylidene or mono- or di-substituted fluoren-9-ylidene, wherein said fluoren-9-ylidene substituents are each independently $C_1$-$C_{12}$ alkyl, $C_1$-$C_{12}$ alkoxy or halogen;

$R^{13}$ and $R^{14}$ are each independently:
(a) a metallocenyl group;

(b) a reactive substituent or a compatiblizing substituent;

(c) perhalo($C_1$-$C_{10}$)alkyl, a perhalo($C_2$-$C_{10}$)alkenyl, a perhalo($C_3$-$C_{10}$)alkynyl, a perhalo($C_1$-$C_{10}$)alkoxy or a perhalo($C_3$-$C_{10}$)cycloalkyl;

(d) a group represented by —O(CH$_2$)$_a$(CX$_2$)$_b$CT$_3$, wherein T is a halogen, X is hydrogen or halogen, a is an integer ranging from 1 to 10, and b is an integer ranging from 1 to 10;

(e) a silicon-containing group represented by one of

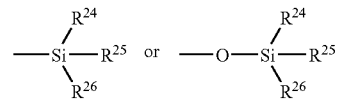

wherein $R^{24}$, $R^{25}$, and $R^{26}$ are each independently $C_1$-$C_{10}$ alkyl, $C_1$-$C_{10}$ alkoxy or phenyl;

(f) hydrogen, hydroxy, $C_1$-$C_6$ alkyl, chloro, fluoro, $C_3$-$C_7$ cycloalkyl, allyl or $C_1$-$C_8$ haloalkyl;

(g) morpholino, piperidino, pyrrolidino, an unsubstituted, mono- or di-substituted amino, wherein said amino substituents are each independently $C_1$-$C_6$ alkyl, phenyl, benzyl or naphthyl;

(h) an unsubstituted, mono-, di- or tri-substituted aryl group chosen from phenyl, naphthyl, benzyl, phenanthryl, pyrenyl, quinolyl, isoquinolyl, benzofuranyl, thienyl, benzothienyl, dibenzofuranyl, dibenzothienyl, carbazolyl or indolyl wherein the aryl group substituents are each independently halogen, $C_1$-$C_6$ alkyl or $C_1$-$C_6$ alkoxy;

(i) —C(=O)$R^{27}$, wherein $R^{27}$ is hydrogen, hydroxy, $C_1$-$C_6$ alkyl, $C_1$-$C_6$ alkoxy, amino, mono- or di-($C_1$-$C_6$)alkylamino, morpholino, piperidino, pyrrolidino, an unsubstituted, mono- or di-substituted phenyl or naphthyl, an unsubstituted, mono- or di-substituted phenoxy, an unsubstituted, mono- or di-substituted phenylamino, wherein said phenyl, naphthyl, phenoxy, and phenylamino substituents are each independently $C_1$-$C_6$ alkyl or $C_1$-$C_6$ alkoxy;

(j) —$OR^{28}$, wherein $R^{28}$ is
(i) $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_8$ chloroalkyl, $C_1$-$C_8$ fluoroalkyl, allyl or $C_1$-$C_6$ acyl,
(ii) —CH($R^{29}$)$R^{30}$, wherein $R^{29}$ is hydrogen or $C_1$-$C_3$ alkyl, and $R^{30}$ is —CN, —CF$_3$ or —COOR$^{13}$, wherein $R^{31}$ is hydrogen or $C_1$-$C_3$ alkyl, or
(iii) —C(=O)$R^{32}$, wherein $R^{32}$ is hydrogen, $C_1$-$C_6$ alkyl, $C_1$-$C_6$ alkoxy, amino, mono- or di-($C_1$-$C_6$) alkylamino, an unsubstituted, mono- or di-substituted phenyl or naphthyl, an unsubstituted, mono- or di-substituted phenoxy or an unsubstituted, mono- or di-substituted phenylamino, wherein said phenyl, naphthyl, phenoxy and phenylamino substituents are each independently $C_1$-$C_6$ alkyl or $C_1$-$C_6$ alkoxy;

(k) a 4-substituted phenyl, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$— or —[O—(CH$_2$)$_e$]$_f$—, wherein e is an integer ranging from 2 to 6 and f is an integer ranging from 1 to 50, and wherein the substituent is connected to an aryl group on another photochromic material;
(l) —CH($R^{33}$)$_2$, wherein $R^{33}$ is —CN or —COOR$^{34}$, wherein $R^{34}$ is hydrogen, $C_1$-$C_6$ alkyl, $C_3$-$C_7$ cycloalkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl or an unsubstituted, mono- or di-substituted phenyl or naphthyl, wherein said phenyl and naphthyl substituents are each independently $C_1$-$C_6$ alkyl or $C_1$-$C_6$ alkoxy;
(m) —CH($R^{35}$)$R^{36}$, wherein $R^{35}$ is hydrogen, $C_1$-$C_6$ alkyl or an unsubstituted, mono- or di-substituted phenyl or naphthyl, wherein said phenyl and naphthyl substituents are each independently $C_1$-$C_6$ alkyl or $C_1$-$C_6$ alkoxy, and $R^{36}$ is —C(=O)OR$^{37}$, —C(=O)R$^{38}$ or —CH$_2$OR$^{39}$, wherein
  (i) $R^{37}$ is hydrogen, $C_1$-$C_6$ alkyl, $C_3$-$C_7$ cycloalkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl or an unsubstituted, mono- or di-substituted phenyl or naphthyl, wherein said phenyl and naphthyl substituents are each independently $C_1$-$C_6$ alkyl or $C_1$-$C_6$ alkoxy,
  (ii) $R^{36}$ is hydrogen, $C_1$-$C_6$ alkyl, amino, mono($C_1$-$C_6$)alkylamino, di($C_1$-$C_6$) alkylamino, phenylamino, diphenylamino, (mono- or di-($C_1$-$C_6$)alkyl substituted phenyl)amino, (mono- or di-($C_1$-$C_6$) alkoxy substituted phenyl)amino, di(mono- or di-($C_1$-$C_6$)alkyl substituted phenyl)amino, di(mono- or di-($C_1$-$C_6$)alkoxy substituted phenyl)amino, morpholino, piperidino or an unsubstituted, mono- or di-substituted phenyl or naphthyl, wherein said phenyl and naphthyl substituents are each independently $C_1$-$C_6$ alkyl or $C_1$-$C_6$ alkoxy, and
  (iii) $R^{39}$ is hydrogen, —C(=O)R$^{37}$, $C_1$-$C_6$ alkyl, $C_1$-$C_3$ alkoxy ($C_1$-$C_6$)alkyl, phenyl($C_1$-$C_6$)alkyl, mono-alkoxy substituted phenyl($C_1$-$C_6$)alkyl or an unsubstituted, mono- or di-substituted phenyl or naphthyl, wherein said phenyl or naphthyl substituents are each independently $C_1$-$C_6$ alkyl or $C_1$-$C_6$ alkoxy; or
$R^{13}$ and $R^{14}$ together form an oxo group, a spiro-carbocyclic group containing 3 to 6 carbon atoms or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings;
$R^6$, $R^8$, $R^9$ and $R^{12}$ are each independently:
  (a) hydrogen, $C_1$-$C_6$ alkyl, chloro, fluoro, bromo, $C_3$-$C_7$ cycloalkyl or an unsubstituted, mono- or di-substituted phenyl, wherein said phenyl substituents are each independently $C_1$-$C_6$ alkyl or $C_1$-$C_6$ alkoxy;
  (b) —OR$^{40}$ or —OC(=O)R$^{40}$ wherein R$^{40}$ is hydrogen, amine, alkylene glycol, polyalkylene glycol, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$alkyl, $C_3$-$C_7$ cycloalkyl, mono($C_1$-$C_4$alkyl substituted $C_3$-$C_7$ cycloalkyl or an unsubstituted, mono- or di-substituted phenyl, wherein said phenyl substituents are each independently $C_1$-$C_6$ alkyl or $C_1$-$C_6$ alkoxy;
  (c) a reactive substituent or a compatiblizing substituent;
  (d) a 4-substituted phenyl, the substituent being a dicarboxylic acid residue or derivative thereof, a diamine residue or derivative thereof, an amino alcohol residue or derivative thereof, a polyol residue or derivative thereof, —(CH$_2$)—, —(CH$_2$)$_e$— or —[O—(CH$_2$)$_e$]$_f$—, wherein e is an integer ranging from 2 to 6, and f is an integer ranging from 1 to 50, and wherein the substituent is connected to an aryl group on another photochromic material;
  (e) —N($R^{41}$)$R^{42}$, wherein $R^{41}$ and $R^{42}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_8$ cycloalkyl, $C_4$-$C_{16}$ bicycloalkyl, $C_5$-$C_{20}$ tricycloalkyl or $C_1$-$C_{20}$ alkoxy($C_1$-$C_6$)alkyl, or $R^{41}$ and $R^{42}$ come together with the nitrogen atom to form a $C_3$-$C_{20}$ hetero-bicycloalkyl ring or a $C_4$-$C_{20}$ hetero-tricycloalkyl ring;
  (f) a nitrogen containing ring represented by:

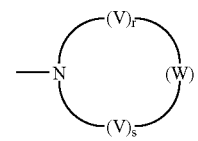

wherein each —V— is independently chosen for each occurrence from —CH$_2$—, —CH($R^{43}$)—, —C($R^{43}$)$_2$—, —CH(aryl)—, —C(aryl)$_2$- and —C($R^{43}$)(aryl)-, wherein each $R^{43}$ is independently $C_1$-$C_6$ alkyl and each aryl is independently phenyl or naphthyl; —W— is —V—, —O—, —S—, —S(O)—, —SO$_2$—, —NH—, —N($R^{43}$)— or —N(aryl)-; s is an integer ranging from 1 to 3; and r is an integer ranging from 0 to 3, provided that if r is 0 then —W— is the same as —V—;
  (g) a group represented by:

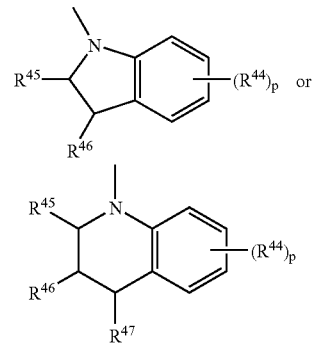

wherein each $R^{44}$ is independently $C_1$-$C_6$ alkyl, $C_1$-$C_6$ alkoxy, fluoro or chloro; $R^{46}$, $R^{46}$ and $R^{47}$ are each independently hydrogen, $C_1$-$C_6$ alkyl, phenyt or naphthyl, or $R^{45}$ and $R^{46}$ together form a ring of 5 to 8 carbon atoms; and p is an integer ranging from 0 to 3; or
  (h) a substituted or an unsubstituted $C_4$-$C_{18}$ spirobicyclic amine or a substituted or an unsubstituted $C_4$-$C_{18}$ spirotricyclic amine, wherein said substituents are each independently aryl, $C_1$-$C_6$ alkyl, $C_1$-$C_6$ alkoxy or phenyl($C_1$-$C_6$)alkyl;
$R^7$ and $R^{10}$ are each independently:
  (a) any of the groups discussed above with respect to $R^5$, $R^8$, $R^9$ and $R^{12}$; or
  (b) a metallocenyl group;
$R^6$ and $R^{11}$ are each independently:
  (a) any of the groups discussed above with respect to $R^7$ and $R^{10}$;
  (b) perfluoroalkyl or perfluoroalkoxy;

(c) -O(=O)$R^{46}$ or -SO2$R^{48}$ wherein each $R^{46}$ is independently hydrogen, $C_1$-$C_6$ alkyl, —$OR^{49}$ or —$NR^{50}R^{51}$, wherein $R^{49}$, $R^{50}$ and $R^{51}$ are each independently hydrogen, $C_1$-$C_6$ alkyl, $C_5$-$C_7$ cycloalkyl, alkylene glycol, polyalkylene glycol or an unsubstituted, mono- or di-substituted phenyl, wherein said phenyl substituents are each independently $C_1$-$C_6$ alkyl or $C_1$-$C_6$ alkoxy;

(d) —C(=C($R^{52}$)$_2$)$R^{53}$, wherein each $R^{52}$ is independently —O(=O)$R^{48}$, —$OR^{49}$, —OC(=O)$R^{49}$, —$NR^{50}R^{51}$, hydrogen, halogen, cyano, $C_1$-$C_6$ alkyl, $C_5$-$C_7$ cycloalkyl, alkylene glycol, polyalkylene glycol or an unsubstituted, mono- or di-substituted phenyl, wherein said phenyl substituents are each independently $C_1$-$C_6$ alkyl or $C_1$-$C_6$ alkoxy, and $R^{53}$ is hydrogen, $C_1$-$C_6$ alkyl, $C_5$-$C_7$ cycloalkyl, alkylene glycol, polyalkylene glycol or an unsubstituted, mono- or di-substituted phenyl, wherein said phenyl substituents are each independently $C_1$-$C_6$ alkyl or $C_1$-$C_6$ alkoxy; or (e) —C≡C$R^{54}$ or —C≡N wherein $R^{54}$ is —C(=O)$R^{46}$, hydrogen, $C_1$-$C_6$ alkyl, $C_5$-$C_7$ cycloalkyl or an unsubstituted, mono- or di-substituted phenyl, wherein said phenyl substituents are each independently $C_1$-$C_6$ alkyl or $C_1$-$C_6$ alkoxy; or a least one pair of adjacent groups $R^6$ and $R^7$ or $R^{10}$ and $R^{11}$ together form a group represented by:

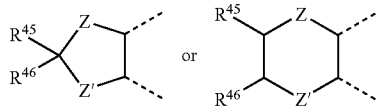

wherein Z and Z' are each independently oxygen or the group —$NR^{41}$—; or $R^6$ and $R^7$ or $R^{10}$ and $R^{11}$ together form an aromatic or heteroaromatic fused group, said fused group being benzo, indeno, dihydronaphthatene, indole, benzofuran, benzopyran or thianaphthene; provided that the photochromic material comprises at least one metallocenyl group.

14. The photochromic material of claim 13 wherein at least one of $R^6$, $R^7$, $R^{10}$, $R^{11}$, $R^{13}$ or $R^{14}$ is a metallocenyl group.

15. The photochromic material of claim 13 wherein the metallocenyl group is at least one of a ferrocenyl group, a titanocenyl group, a ruthenocenyl group and a chromocenyl group.

16. A photochromic indeno[2',3':3,4]naphtho[1,2-b]pyran comprising a metalbocenyl group bonded to at least one of the 6-position, the 7-position, the 11-position or the 13-position of the indenol[2',3':3,4]naphtho[1,2-b]pyran.

17. The photochromic material of claim 16 wherein the metallocenyl group comprises a first cyclopentadienyl ring and a second cyclopentadienyl ring, and wherein the first cyclopentadienyl ring of the metallocenyl group is bonded to at least one of the 6-position, the 7-position, the 11-position or the 13-position of the indeno[2',3':3,4]naphtho [1,2-b]pyran and the second cyclopentadienyl ring is bonded to a corresponding position on another indeno[2',3':3,4]naphthol[1,2-b]pyran.

* * * * *